(12) United States Patent
Takahashi et al.

(10) Patent No.: US 8,058,247 B2
(45) Date of Patent: Nov. 15, 2011

(54) ANTIBACTERIAL AGENT AND THERAPEUTIC AGENT FOR JOHNE'S DISEASE CONTAINING THE SAME

(75) Inventors: Yoshiaki Takahashi, Tokyo (JP); Masayuki Igarashi, Tokyo (JP)

(73) Assignees: Microbial Chemistry Research Foundation, Tokyo (JP); Meiji Seika Kaisha, Ltd., Tokyo (JP)

( * ) Notice: Subject to any disclaimer, the term of this patent is extended or adjusted under 35 U.S.C. 154(b) by 354 days.

(21) Appl. No.: 12/378,172

(22) Filed: Feb. 11, 2009

(65) Prior Publication Data

US 2009/0209744 A1    Aug. 20, 2009

Related U.S. Application Data

(63) Continuation of application No. PCT/JP2007/065606, filed on Aug. 9, 2007.

(30) Foreign Application Priority Data

Aug. 15, 2006   (JP) .................... 2006-221723

(51) Int. Cl.
  *A61K 31/7016*  (2006.01)
  *A61K 31/7052*  (2006.01)
  *C07G 11/00*  (2006.01)
  *C07H 15/26*  (2006.01)
(52) U.S. Cl. .................. 514/32; 536/16.8; 536/17.4
(58) Field of Classification Search .......... None
  See application file for complete search history.

(56) References Cited

U.S. PATENT DOCUMENTS 7,482,439 B2 *  1/2009  Miyake et al. ............ 536/16.8

FOREIGN PATENT DOCUMENTS

| WO | 97/41248 | 11/1997 |
| WO | 2004/067544 | 8/2004 |

OTHER PUBLICATIONS

Cocito, C. et al; Paratuberculosis; Clinical Microbiology Reviews, vol. 7, No. 3, pp. 328-345, Jul. 1994.
Van Schaik, G. et al; Cost -Benefit Analysis of Vaccination Against Paratuberculosis in Dairy Cattle; Veterinary Record 139, pp. 624-627, Dec. 21/28, 1996.
Molina, J.M. et al; Study on Immune Response of Goats Vaccinated with a Live Strain of *Mycobacterium paratuberculosis*; Comp. Immun. Microbiol. Infect. Dis., vol. 19, No. 1, pp. 9-15, 1996.

* cited by examiner

*Primary Examiner* — Eric S Olson
(74) *Attorney, Agent, or Firm* — Carmody & Torrance LLP

(57) ABSTRACT

An antibacterial agent having high antibacterial activity against *Mycobacterium avium* subsp. *paratuberculosis* is provided. Specifically, the antibacterial agent of the present invention having high antibacterial activity against *Mycobacterium avium* subsp. *paratuberculosis* is a caprazamycin derivative represented, for example, by the following general formula (II):

wherein Me is a methyl group; and $R^1$ is a straight or substantially straight chain alkyl group having 5 to 21 carbon atoms, a straight or substantially straight chain alkenyl group having 5 to 21 carbon atoms, a cycloalkyl group having 5 to 12 carbon atoms, or a phenyl group substituted at the para-position with a straight chain alkyl group having 1 to 14 carbon atoms, a straight chain alkoxy group having 1 to 9 carbon atoms or a cycloalkyl group having 5 to 12 carbon atoms.

19 Claims, No Drawings

ANTIBACTERIAL AGENT AND THERAPEUTIC AGENT FOR JOHNE'S DISEASE CONTAINING THE SAME

CROSS-REFERENCE TO RELATED APPLICATIONS

This is a continuation of Application No. PCT/JP2007/065606, flied on Aug. 9, 2007, which claims priority from JP2006-221723 filed on Aug. 15, 2006.

BACKGROUND OF THE INVENTION

1. Field of the Invention

The present invention relates to an antibacterial agent effective against *Mycobacterium avium* subsp. *paratuberculosis*, and to a therapeutic agent for Johne's disease containing the antibacterial agent.

2. Description of the Related Art

Johne's disease is a contagious disease that affects cattle, sheep and other ruminants. The disease is caused by *Mycobacterium avium* subsp. *paratuberculosis*, an acid-fast bacillus, and is orally transmitted from one animal to another. Among major symptoms of the disease are chronic enteritis and a significant reduction in body weight. In Japan, Johne's disease was designated as a legal communicable disease in 1971. The disease has an extremely long course and may remain latent for one to several years, in some cases for as long as 10 years, before it develops. Asymptomatically-infected cattle excrete a large number of bacteria in their feces that can infect other animals in the herd (See, C. Cocito, P. Gilot, M. Coene, M. de Kesel, P. Poupart, and P. Vannuffel; *Paratuberculosis*; Clinical Microbiology Reviews, vol. 7, No. 3, pp 328-345 (1994)).

One approach to counteract Johne's disease is vaccination by subcutaneous injection of inactivated Johne's disease bacteria with an oil adjuvant (van Schaik G, Kalis C H, Benedictus G, Dijkhuizen A A, Huirne R B, Cost-benefit analysis of vaccination against *paratuberculosis* in dairy cattle. Vet Rec 139: 624-7 (1996), and Molina J M, Anguiano A, Ferrer O, Study on immune response of goats vaccinated with a live strain of *Mycobacterium paratuberculosis*. Comp Immunol Microbiol Infect Dis 19: 9-15 (1996)). Although vaccination can enhance the cellular immunity after infection, it only suppresses the onset of the disease, rather than prevent infection, resulting in latently infected cattle that continuously excrete bacteria in their feces. Thus, vaccination may not provide a decisive solution, but rather may spread the disease.

With no effective measures presently available for the prevention or treatment of the disease, the most effective way to prevent epidemic is to quickly find and eliminate infected animals. The Act on Domestic Animal Infectious Disease Control in Japan requires that the infected animals be disposed of immediately. Johne's disease can affect a large population of animals and is considered one of the most important diseases that can severely damage the cattle dairy and husbandary industry. The disease can not only cause direct damage to the industry by decreasing the productivity and requiring disposal of affected animals, but can also lead to a significantly increased cost associated with long-term, regular health check-ups and restricted translocation of affected animals.

At present, no effective antibacterial agents against *Mycobacterium avium* subsp. *paratuberculosis* are available, nor are there any therapeutic agents containing such antibacterial agents.

BRIEF SUMMARY OF THE INVENTION

The present invention offers a solution to the above-described problems in the prior art. Accordingly, it is an objective of the present invention to provide an antibacterial agent effective against *Mycobacterium avium* subsp. *paratuberculosis*, as well as a therapeutic agent for Johne's disease containing such an antibacterial agent.

In the course of studies to find a way to solve the above-described problems, the present inventors have found that caprazamycin derivatives, compounds described in a patent application previously filed by the present inventors (See, WO2004/067544 pamphlet), exhibit high antibacterial activity against *mycobacterium avium* subsp. *paratuberculosis*. The present inventors have then considered using the compounds as antibacterial agents against the bacteria and making a therapeutic agent for Johne's disease using these compounds. It is this idea that ultimate lead to the present invention.

The present invention to solve the above-described problems includes the following:

(1) an antibacterial agent having antibacterial activity against *Mycobacterium avium* subsp. *paratuberculosis*, containing a caprazamycin derivative represented by one of the following general formula (II), (III), (V), (VI) or (VII):

(II)

wherein Me is a methyl group; and $R^1$ is a straight or substantially straight chain alkyl group having 5 to 21 carbon atoms, a straight or substantially straight chain alkenyl group having 5 to 21 carbon atoms, a cycloalkyl group having 5 to 12 carbon atoms, a phenyl group substituted at the para-position with a straight chain alkyl group having 1 to 14 carbon atoms, a straight chain alkoxy group having 1 to 9 carbon atoms, or a cycloalkyl group having 5 to 12 carbon atoms;

(III)

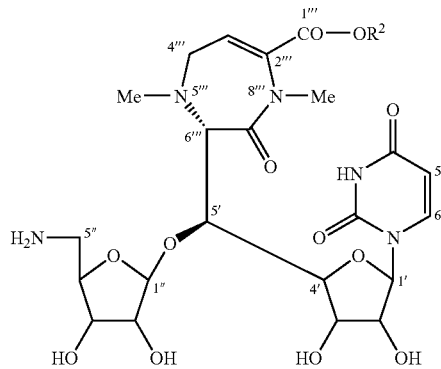

wherein Me is a methyl group; and $R^2$ is a straight or substantially straight chain alkyl group having 5 to 21 carbon atoms, a straight or substantially straight chain alkenyl group having 5 to 21 carbon atoms, or an alkynyl group having 5 to 21 carbon atoms;

(V)

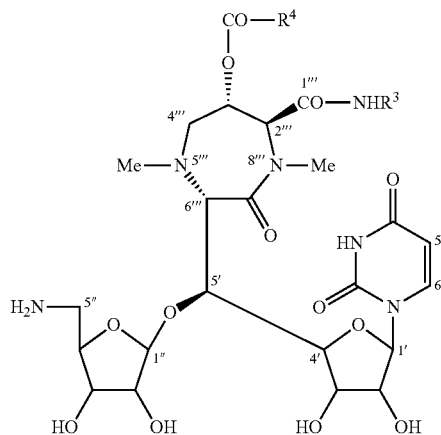

wherein Me is a methyl group; and $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms;

(VI)

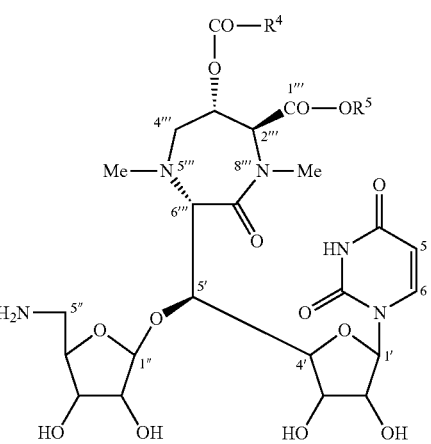

wherein Me is a methyl group; $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms; and $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms; and (VII)

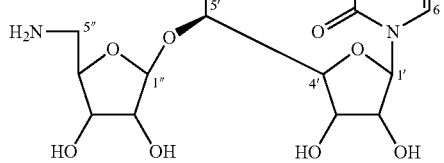

wherein Me is a methyl group; $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms; and $R^5$ is a hydrogen atom, or a straight or substantially straight chain alkyl group having 1 to 21 carbon atoms.

(2) A therapeutic agent for Johne's disease containing the antibacterial agent according to (1) above.

According to the present invention, the above-described problems in the prior art can be solved by the antibacterial agent having high antibacterial activity against *Mycobacterium avium* subsp. *paratuberculosis* or by the therapeutic agent containing the antibacterial agent.

DETAILED DESCRIPTION OF THE INVENTION

Antibacterial Agent

An antibacterial agent of the present invention is a caprazamycin derivative that shows antibacterial activity against *Mycobacterium avium* subsp. *paratuberculosis* and is represented by one of the general formulas (II), (III), (V), (VI) and (VII).

The caprazamycin derivatives represented by the aforementioned general formula (II) and (III) are derivatives of caprazene represented by the following formula (I):

(I)

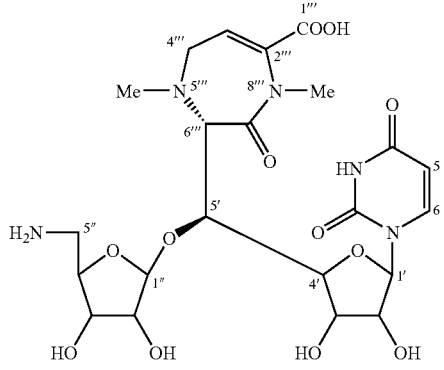

where Me is a methyl group. Caprazene is derived from at least one of the following caprazamycins:

caprazamycins A, B, C, E and F represented by the following general formula (A):

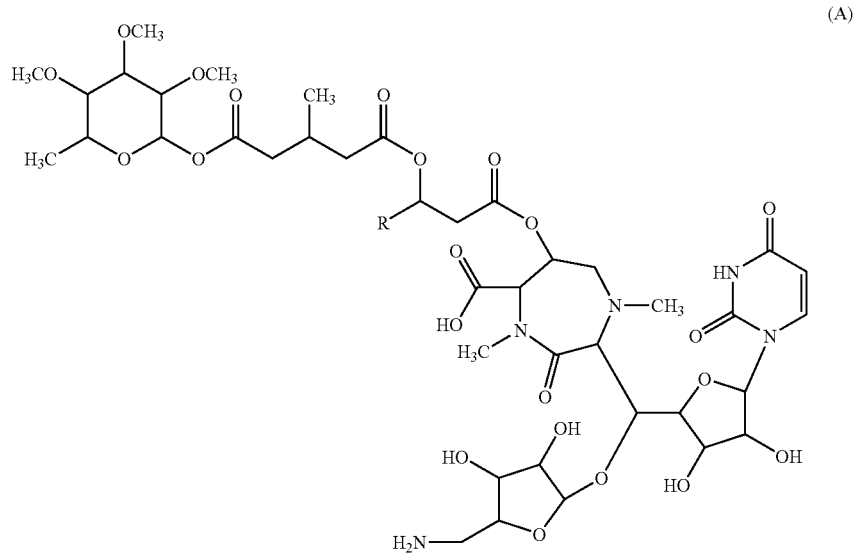

(A)

(wherein R is a tridecyl group in caprazamycin A, a 11-methyl-dodecyl group in caprazamycin B, a dodecyl group in caprazamycin C, a undecyl group in caprazamycin E, and a 9-methyl-decyl group in caprazamycin F);

caprazamycins D and G represented by the following general formula (B):

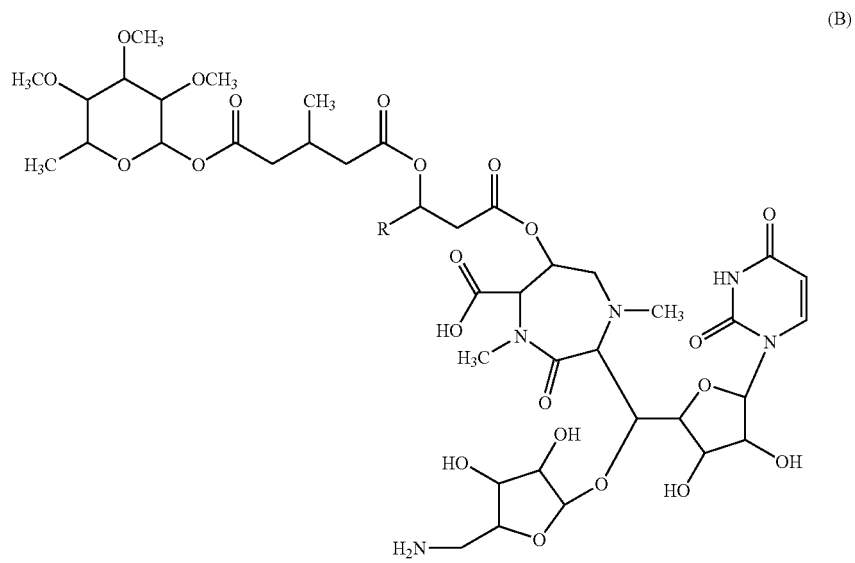

(B)

(wherein R is a 10-methyl-undecyl group ($-(CH_2)_9CH(CH_3)_2$) in caprazamycin D, and a 9-methyl-undecyl group ($-(CH_2)_8CH(CH_3)CH_2CH_3$) in caprazamycin G); and caprazamycins D1 and G1 represented by the following general formula (C):

(C)

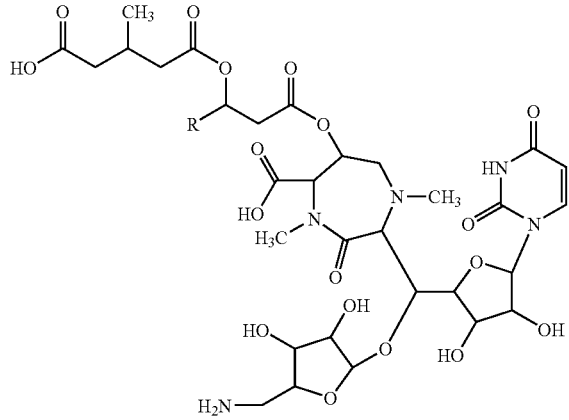

(wherein R is a 10-methyl-undecyl group ($-(CH_2)_9CH(CH_3)_2$) in caprazamycin D1, and a 9-methyl-undecyl group ($-(CH_2)_8CH(CH_3)CH_2CH_3$) in caprazamycin G1).

Although any suitable process may be used to derive caprazene represented by the aforementioned formula (I) from any of caprazamycins A, B, C, E and F represented by the aforementioned formula (A), caprazamycins D and G represented by the aforementioned formula (B) and caprazamycins D1 and G1 represented by the general formula (C), a process described in WO2004/067544 pamphlet is preferably used. Specifically, caprazamycin A, B, C, D, E, F or G or a mixture containing at least two selected from caprazamycins A, B, C, D, E, F and G is treated in an aqueous acid solution either at room temperature or at an elevated temperature.

The caprazamycin derivatives represented by the aforementioned general formula (V), (VI) and (VII) are derivatives of caprazol represented by the following formula (IV):

(IV)

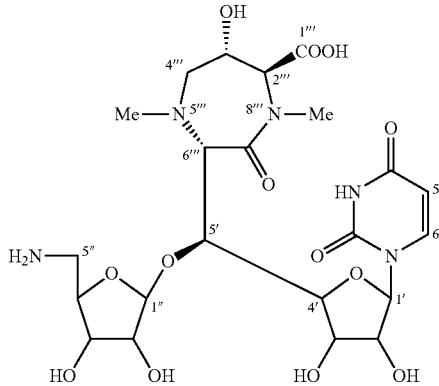

wherein Me is a methyl group. Caprazol is derived from at least one of caprazamycins A, B, C, E and F represented by the aforementioned general formula (A), caprazamycins D and G represented by the aforementioned general formula (B) and caprazamycins D1 and G1 represented by the aforementioned general formula (C).

Although any suitable process may be used to derive caprazol represented by the aforementioned formula (IV) from any of caprazamycins A, B, C, E and F represented by the aforementioned formula (A), caprazamycins D and G represented by the aforementioned formula (B) and caprazamycins D1 and G1 represented by the general formula (C), a process described in WO2004/067544 pamphlet is preferably used. Specifically, caprazamycin A, B, C, D, E, F or G or a mixture containing at least two selected from caprazamycins A, B, C, D, E, F and G is subjected to hydrolysis in an aqueous solution of an inorganic base either at room temperature or at an elevated temperature.

<Caprazamycin Derivative Represented by the General Formula (II)>

Caprazamycin derivatives represented by the following general formula (II) are amide derivatives of caprazene represented by the aforementioned formula (I). Specifically, they are caprazene-1'''-amide derivatives.

(II)

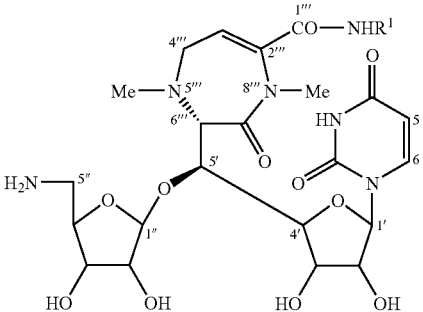

wherein Me is a methyl group; and $R^1$ is a straight or substantially straight chain alkyl group having 5 to 21 carbon atoms, a straight or substantially straight chain alkenyl group having 5 to 21 carbon atoms, a cycloalkyl group having 5 to 12 carbon atoms, or a phenyl group substituted at the para-position with a straight chain alkyl group having 1 to 14 carbon atoms, a straight chain alkoxy group having 1 to 9 carbon atoms or a cycloalkyl group having 5 to 12 carbon atoms.

Examples of the straight chain alkyl group having 5 to 21 carbon atoms include those shown in Table 1 below. Of these, alkyl groups having 8 to 16 carbon atoms are particularly preferred because of high antibacterial activity exhibited by caprazamycin derivatives having these alkyl groups.

TABLE 1

| Alkyl groups | |
|---|---|
| Formula | Name |
| $C_5H_{11}-$ | pentyl(amyl) |
| $C_6H_{13}-$ | hexyl |
| $C_7H_{15}-$ | heptyl |
| $C_8H_{17}-$ | octyl |
| $C_9H_{19}-$ | nonyl |
| $C_{10}H_{21}-$ | decyl |
| $C_{11}H_{23}-$ | undecyl |
| $C_{12}H_{25}-$ | dodecyl |
| $C_{13}H_{27}-$ | tridecyl |
| $C_{14}H_{29}-$ | tetradecyl |
| $C_{15}H_{31}-$ | pentadecyl |
| $C_{16}H_{33}-$ | hexadecyl |
| $C_{17}H_{35}-$ | heptadecyl |
| $C_{18}H_{37}-$ | octadecyl |
| $C_{19}H_{39}-$ | nonadecyl |
| $C_{20}H_{41}-$ | icosyl |
| $C_{21}H_{43}-$ | henicosyl |

Examples of the substantially straight chain alkyl group having 5 to 21 carbon atoms include alkyl groups having 5 to 21 carbon atoms whose straight carbon chain is substituted with 1 to 3 methyl, ethyl or n-propyl groups either at the terminal or at an internal carbon atom. Specific examples of such alkyl groups include 9-methyl-undecyl group ($-(CH_2)_8CH(CH_3)CH_2CH_3$) and 10-methyl-undecyl group ($-(CH_2)_9CH(CH_3)_2$).

Examples of the straight chain alkenyl group having 5 to 21 carbon atoms include pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group and icosenyl group. The double bond of these alkenyl groups may be present either at an internal position of the alkenyl chain or at the α- or ω-carbon atom of the alkenyl chain.

Examples of the substantially straight chain alkenyl group having 5 to 21 carbon atoms include alkenyl groups having 5 to 21 carbon atoms whose straight carbon chain is substituted with 1 to 3 methyl, ethyl or n-propyl groups either at the terminal or at an internal position. Specific examples of such alkenyl groups include 9-methyl-9-undecenyl group ($-(CH_2)_8C(CH_3)=CHCH_3$) and 10-methyl-9-undecenyl group ($-(CH_2)_8CH=C(CH_3)_2$).

Examples of the cycloalkyl group having 5 to 12 carbon atoms include cyclopentyl group, cyclohexyl group, cycloheptyl group, cyclooctyl group, cyclononyl group, cyclodecyl group, cycloundecyl group and cyclododecyl group. The cycloalkane ring of these cycloalkyl groups may be substituted with 1 to 3 methyl or ethyl groups.

Examples of the phenyl group substituted at the para-position with a straight chain alkyl group having 1 to 14 carbon atoms, a straight chain alkoxy group having 1 to 9 carbon atoms or a cycloalkyl group having 5 to 12 carbon atoms include those shown as $R^1$ in Tables 3 and 4 below.

Specific examples of the caprazamycin derivatives represented by the aforementioned general formula (II) are presented in Tables 2 to 4 below, along with their respective specific rotations.

TABLE 2

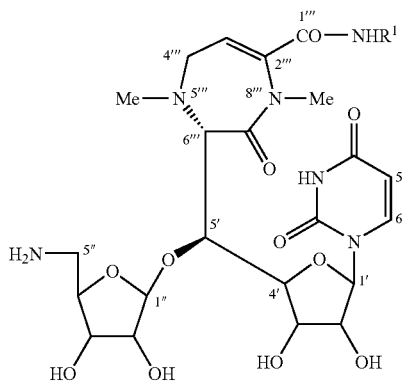

(II)

| Compound codes | $R^1$ in the formula (II) | Specific rotation $[\alpha]_D$ (c 0.5, in water) |
|---|---|---|
| Compound II-A | $-(CH_2)_5CH_3$ | $[\alpha]_D^{20} + 70°$ |
| Compound II-B | $-(CH_2)_6CH_3$ | $[\alpha]_D^{21} + 72°$ |
| Compound II-C | $-(CH_2)_7CH_3$ | $[\alpha]_D^{20} + 72°$ |
| Compound II-D | $-(CH_2)_8CH_3$ | $[\alpha]_D^{20} + 73°$ |
| Compound II-E | $-(CH_2)_9CH_3$ | $[\alpha]_D^{21} + 72°$ |
| Compound II-F | $-(CH_2)_{10}CH_3$ | $[\alpha]_D^{20} + 73°$ |
| Compound II-G | $-(CH_2)_{11}CH_3$ | $[\alpha]_D^{21} + 72°$ |
| Compound II-H | $-(CH_2)_{12}CH_3$ | $[\alpha]_D^{20} + 72°$ |
| Compound II-I | $-(CH_2)_{13}CH_3$ | $[\alpha]_D^{20} + 68°$ |
| Compound II-J | $-(CH_2)_{14}CH_3$ | $[\alpha]_D^{21} + 66°$ |
| Compound II-K | $-(CH_2)_{15}CH_3$ | $[\alpha]_D^{20} + 67°$ |
| Compound II-L | $-(CH_2)_{16}CH_3$ | $[\alpha]_D^{20} + 67°$ |
| Compound II-M | $-(CH_2)_{17}CH_3$ | $[\alpha]_D^{20} + 66°$ |
| Compound II-N | $-(CH_2)_{18}CH_3$ | $[\alpha]_D^{20} + 60°$ |
| Compound II-O | $-(CH_2)_{19}CH_3$ | $[\alpha]_D^{20} + 60°$ |
| Compound II-P | $-(CH_2)_{20}CH_3$ | $[\alpha]_D^{20} + 60°$ |
| Compound II-Q | cyclododecyl | $[\alpha]_D^{20} + 71°$ |
| Compound II-R | oleyl $-(CH_2)_8CH=CH(CH_2)_7CH_3$ (cis form) | $[\alpha]_D^{20} + 64°$ |

TABLE 3

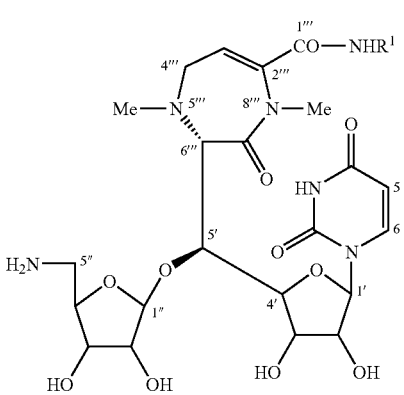

(II)

| Compound codes | $R^1$ in the formula (II) | Specific rotation $[\alpha]_D^{22}$ (c 0.5, in methanol) |
|---|---|---|
| Compound II-1 |  —CH$_3$ | +81° |

TABLE 3-continued (II)

[Structure of formula (II) showing a macrocyclic compound with uridine base, two furanose rings (with positions 1', 4', 5' and 1", 5"), a diazepine-containing ring with positions 1''', 2''', 4''', 5''', 6''', 8''', bearing CO—NHR¹, Me groups on N5''' and N8''', H₂N—CH₂ at 5", and OH groups on both sugars]

| Compound codes | R¹ in the formula (II) | Specific rotation $[\alpha]_D^{22}$ (c 0.5, in methanol) |
|---|---|---|
| Compound II-2 | —C₆H₄—CH₂CH₃ (para) | +80° |
| Compound II-3 | —C₆H₄—(CH₂)₂CH₃ (para) | +78° |
| Compound II-4 | —C₆H₄—(CH₂)₃CH₃ (para) | +76° |
| Compound II-5 | —C₆H₄—(CH₂)₄CH₃ (para) | +74° |
| Compound II-6 | —C₆H₄—(CH₂)₅CH₃ (para) | +73° |
| Compound II-7 | —C₆H₄—(CH₂)₆CH₃ (para) | +72° |
| Compound II-8 | —C₆H₄—(CH₂)₇CH₃ (para) | +71° |
| Compound II-9 | —C₆H₄—(CH₂)₈CH₃ (para) | +69° |
| Compound II-10 | —C₆H₄—(CH₂)₉CH₃ (para) | +67° |
| Compound II-11 | —C₆H₄—(CH₂)₁₀CH₃ (para) | +67° |
| Compound II-12 | —C₆H₄—(CH₂)₁₁CH₃ (para) | +66° |

TABLE 3-continued (II)

| Compound codes | R¹ in the formula (II) | Specific rotation $[\alpha]_D^{22}$ (c 0.5, in methanol) |
|---|---|---|
| Compound II-13 | —C₆H₄—(CH₂)₁₂CH₃ | +66° |
| Compound II-14 | —C₆H₄—(CH₂)₁₃CH₃ | +64° |

TABLE 4

(II)

| Compound codes | R¹ in the formula (II) | Specific rotation $[\alpha]_D^{22}$ (c 0.5, in methanol) |
|---|---|---|
| Compound II-15 | —C₆H₄—OCH₃ | +80° |
| Compound II-16 | —C₆H₄—OCH₂CH₃ | +80° |
| Compound II-17 | —C₆H₄—O(CH₂)₂CH₃ | +80° |
| Compound II-18 | —C₆H₄—O(CH₂)₃CH₃ | +81° |

TABLE 4-continued

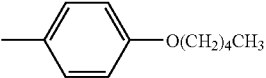

(II)

| Compound codes | R¹ in the formula (II) | Specific rotation $[\alpha]_D^{22}$ (c 0.5, in methanol) |
|---|---|---|
| Compound II-19 | 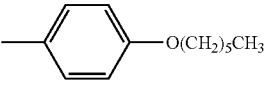—⟨phenyl⟩—O(CH$_2$)$_4$CH$_3$ | +77° |
| Compound II-20 | —⟨phenyl⟩—O(CH$_2$)$_5$CH$_3$ | +78° |
| Compound II-21 | —⟨phenyl⟩—O(CH$_2$)$_6$CH$_3$ | +76° |
| Compound II-22 | —⟨phenyl⟩—O(CH$_2$)$_7$CH$_3$ | +76° |
| Compound II-23 | —⟨phenyl⟩—O(CH$_2$)$_8$CH$_3$ | +74° |
| Compound II-24 | —⟨phenyl⟩—⟨cyclohexyl⟩ | +76° |

(Production Process of Caprazamycin Derivatives Represented by the General Formula (II))

Although the caprazamycin derivatives represented by the aforementioned general formula (II) may be produced using any suitable known process, they are preferably produced as follows: First, caprazene represented by the aforementioned formula (I) is suspended in a mixture of water and dioxane. Triethylamine is then added to the suspension to form a uniform solution of caprazene. To the caprazene solution, an alkoxycarbonylating reagent or an aralkyloxycarbonylating reagent commonly used in the field of organic chemistry for the purpose of protecting amino group is added and the reaction is carried out at room temperature. The resulting reaction mixture contains 5"-N-alkoxycarbonyl- or 5"-N-aralkyloxycarbonyl-caprazene. The reaction mixture is concentrated and the resulting solid residue is washed with ethyl acetate and dried to give desired 5"-N-alkoxycarbonyl- or 5"-N-aralkyloxycarbonyl-caprazene as a solid (hereinafter, these products may be collectively referred to as "5"-N-protected caprazene").

Subsequently, the 5"-N-protected caprazene is either dissolved in pyridine to form a solution, or suspended in tetrahydrofuran (THF) to form a suspension. In the latter case, triethylamine is added to the THF suspension. Then, in the pyridine solution or THF suspension of 5"-N-protected caprazene, an amine compound represented by the general formula (XI) below is reacted with the carboxyl group at the 2''' position of the 5"-N-protected caprazene. This can be done by using a common process for the amidation of carboxylic acids. The amidation process may be conveniently carried out at room temperature after adding N,N-bis(2-oxo-3-oxazolidinyl)phosphinic chloride to activate the carboxyl group.

$$R^1—NH_2 \quad (XI)$$

wherein R¹ is as defined for the aforementioned general formula (II).

The reaction mixture resulting from the amidation process is concentrated and the resulting syrup-like concentrate is extracted with chloroform. The chloroform extract is then washed with water and concentrated to obtain a residue containing a desired 5"-N-protected caprazene-1'''-amide derivative. The residue is dissolved in chloroform and the solution is subjected to silica gel column chromatography for purification using a mixed solvent of chloroform-methanol (10:1) as a developing solvent. The eluted fraction containing the desired product is collected and concentrated to give 5"-N-protected caprazene-1'''-amide derivative as a solid.

The so-obtained 5"-N-protected caprazene-1'''-amide derivative is treated by a common process for the elimination of amino-protecting groups to eliminate the 5"-N-protecting group and to thus give a caprazene-1'''-amide derivative of the aforementioned general formula (II). For example, when the amino-protecting group is a tertiary butoxycarbonyl (Boc) group, it is convenient to dissolve the 5"-N-protected caprazene-1'''-amide derivative in methanol containing 80% trifluoroacetic acid (TFA) and stir the solution at room temperature. The resulting reaction mixture is concentrated and diethyl ether is added to the syrup-like concentrate to form a precipitate. The precipitate is then collected by filtration, washed with diethyl ether and dried to give an addition salt of bis-trifluoroacetic acid of caprazene-1'''-amide derivative of the aforementioned general formula (II) as a solid.

While the caprazamycin derivatives represented by the aforementioned general formula (II) exhibit antibacterial activity against a wide range of bacteria and may preferably be used as antibacterial agents against bacteria in general, they are particularly useful as antibacterial agents against *Mycobacterium avium* subsp. *paratuberculosis*.

<Caprazamycin Derivative Represented by the General Formula (III)>

Caprazamycin derivatives represented by the following general formula (III) are ester derivatives of caprazene represented by the aforementioned formula (I). Specifically, they are caprazene-1'''-ester derivatives.

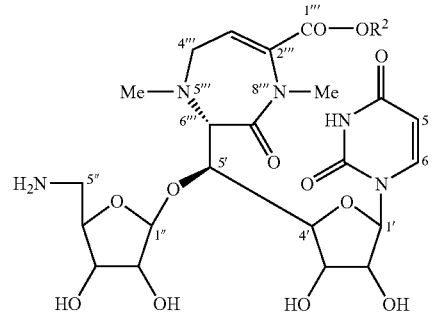

(III)

wherein Me is a methyl group; and $R^2$ is a straight or substantially straight chain alkyl group having 5 to 21 carbon atoms, a straight or substantially straight chain alkenyl group having 5 to 21 carbon atoms, or an alkynyl group having 5 to 21 carbon atoms.

The details of the straight or substantially straight alkyl or alkenyl group having 5 to 21 carbon atoms are as defined for those represented by $R^1$ in the aforementioned general formula (II).

Examples of the alkynyl group having 5 to 21 carbon atoms include pentynyl group, hexynyl group, heptynyl group, octynyl group, nonynyl group and decynyl group.

Specific examples of the caprazamycin derivatives represented by the aforementioned general formula (III) are presented in Tables 5 below, along with their respective specific rotations.

TABLE 5

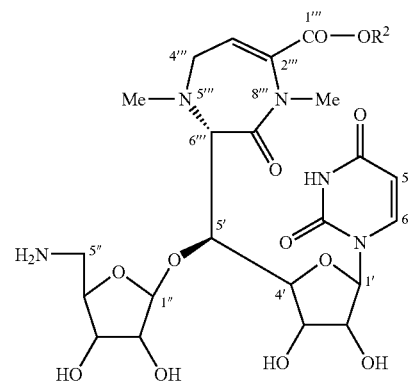

(III)

| Compound codes | $R^2$ in the formula (III) | Specific rotation $[\alpha]_D^{19}$ (c 0.5, in water) |
|---|---|---|
| Compound III-AA | —(CH$_2$)$_9$CH$_3$ | +46° |
| Compound III-BB | —(CH$_2$)$_{12}$CH$_3$ | +50° |
| Compound III-CC | —(CH$_2$)$_{17}$CH$_3$ | +44° |
| Compound III-DD | —(CH$_2$)$_{10}$—CH=CH—CH$_2$—CH$_3$ | +42° |
| Compound III-EE | —CH$_2$—CH=CH—(CH$_2$)$_8$—CH$_3$ | +48° |
| Compound III-FF | —(CH$_2$)$_9$—CH=CH$_2$ | +48° |
| Compound III-GG | —(CH$_2$)$_2$—C≡C—(CH$_2$)$_5$—CH$_3$ | +40° |

(Production Process of Caprazamycin Derivatives Represented by the General Formula (III))

Although the caprazamycin derivatives represented by the aforementioned general formula (III) may be produced using any suitable known process, they are preferably produced as follows: First, 5"-N-alkoxycarbonyl- or 5"-N-aralkyloxycarbonyl-caprazene is prepared as described above in the production process of caprazamycin derivatives of the aforementioned general formula (II). The 5"-N-protected caprazene is then dissolved in pyridine. In the resulting pyridine solution of 5"-N-protected caprazene, an alcohol compound represented by the general formula (XII) below is reacted with the carboxyl group at the 2'" position of the 5"-N-protected caprazene. This can be done by using a common process for the esterification of carboxylic acids. The esterification process may be conveniently carried out at room temperature in the presence of N,N-bis(2-oxo-3-oxazolidinyl)phosphinic chloride.

(XII)

wherein $R^2$ is as defined in the aforementioned general formula (III).

The reaction mixture resulting from the esterification process is concentrated and the resulting concentrate is extracted with chloroform. The chloroform extract is then washed with water and concentrated to obtain a residue containing a desired 5"-N-protected caprazene-1'"-ester derivative. The residue is dissolved in chloroform and the solution is subjected to silica gel column chromatography for purification using a mixed solvent of chloroform-methanol as a developing solvent. The eluted fraction containing the desired product is collected and concentrated to give 5"-N-protected caprazene-1'"-ester derivative as a solid.

The so-obtained 5"-N-protected caprazene-1'"-ester derivative is treated by a common process for the elimination of amino-protecting groups to eliminate the 5"-N-protecting group and to thus give a caprazene-1'"-ester derivative of the aforementioned general formula (III). For example, when the 5"-N-protecting group is a Boc group, it can be conveniently eliminated by dissolving the 5"-N-protected caprazene-1'"-ester derivative in methanol containing 80% TFA and stirring the solution at room temperature. The resulting reaction mixture is concentrated and diethyl ether is added to the concentrate to form a precipitate. The precipitate is then collected by filtration, washed with diethyl ether and dried to give an addition salt of bis-trifluoroacetic acid of caprazene-1'"-ester derivative of the aforementioned general formula (III) as a solid.

While the caprazamycin derivatives represented by the aforementioned general formula (III) exhibit antibacterial activity against a wide range of bacteria and may preferably be used as antibacterial agents against bacteria in general, they are particularly useful as antibacterial agents against *Mycobacterium avium* subsp. *paratuberculosis*.

<Caprazamycin Derivative Represented by the General Formula (V)>

Caprazamycin derivatives represented by the following general formula (V) are amide derivatives of caprazol represented by the aforementioned formula (IV). Specifically, they are caprazol-1'"-amide derivatives.

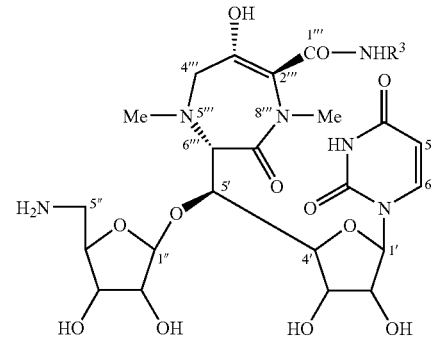

(V)

wherein Me is a methyl group; and $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms. The details of $R^3$ are as defined for $R^1$ in the aforementioned general formula (II).

Specific examples of the caprazamycin derivatives represented by the aforementioned general formula (V) are presented in Tables 6 below, along with their respective specific rotations.

TABLE 6

(V)

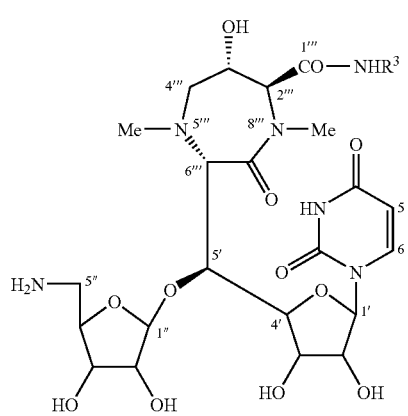

| Compound codes | $R^3$ in the formula (V) | Specific rotation $[\alpha]_D^{19}$ (c 0.5, in methanol) |
|---|---|---|
| Compound V-A | —$(CH_2)_5CH_3$ | +15° |
| Compound V-B | —$(CH_2)_6CH_3$ | |
| Compound V-C | —$(CH_2)_7CH_3$ | +15° |
| Compound V-D | —$(CH_2)_8CH_3$ | |
| Compound V-E | —$(CH_2)_9CH_3$ | +12° |
| Compound V-F | —$(CH_2)_{10}CH_3$ | +12° |
| Compound V-G | —$(CH_2)_{11}CH_3$ | +12° |
| Compound V-Q | cyclododecyl | +35° |
| Compound V-R | oleyl —$(CH_2)_8CH=CH(CH_2)_7CH_3$ (cis form) | +14° |

(Production Process of Caprazamycin Derivatives Represented by the General Formula (V))

Although the caprazamycin derivatives represented by the aforementioned general formula (V) may be produced using any suitable known process, they are preferably produced as follows: First, caprazol represented by the aforementioned formula (IV) is dissolved in water. To the aqueous solution of caprazol, an alkoxycarbonylating reagent or an aralkyloxycarbonylating reagent commonly used in the field of organic chemistry for the purpose of protecting amino group is added, along with triethylamine, and the reaction is carried out at room temperature. When necessary, the alkoxycarbonylating reagent or aralkyloxycarbonylating reagent may be dissolved in an organic solvent such as dioxane prior to the addition to the caprazol solution. The resulting reaction mixture contains 5"-N-alkoxycarbonyl- or 5"-N-aralkyloxycarbonyl-caprazol. The reaction mixture is concentrated and the resulting solid residue is washed with ethyl acetate and dried to give desired 5"-N-alkoxycarbonyl- or 5"-N-aralkyloxycarbonyl-caprazol as a solid (hereinafter, these products may be collectively referred to as "5"-N-protected caprazol").

Subsequently, the 5"-N-protected caprazol is dissolved in N,N-dimethylformamide and triethylamine is added to form a uniform solution of 5"-N-protected caprazol. In this solution, an amine compound represented by the general formula (XIII) below is reacted with the carboxyl group at the 2''' position of the 5"-N-protected caprazol. This can be done by using a common process for the amidation of carboxylic acids. The amidation process may be conveniently carried out at room temperature in the presence of N,N-bis(2-oxo-3-oxazolidinyl)phosphinic chloride.

$$R^3—NH_2 \quad (XIII)$$

wherein $R^3$ is as defined for the aforementioned general formula (V).

The reaction mixture resulting from the amidation process is concentrated and the resulting syrup-like concentrate is extracted with chloroform. The chloroform extract is then washed with water and concentrated to obtain a residue containing a desired 5"-N-protected caprazol-1'''-amide derivative. The residue is dissolved in chloroform and the solution is subjected to silica gel column chromatography for purification using a mixed solvent of chloroform-methanol-concentrated aqueous ammonia as a developing solvent. The eluted active fractions are collected and concentrated to give 5"-N-protected caprazol-1'''-amide derivative as a solid.

The so-obtained 5"-N-protected caprazol-1'''-amide derivative is treated by a common process for the elimination of amino-protecting groups to eliminate the 5"-N-protecting group and to thus give a caprazol-1'''-amide derivative of the aforementioned general formula (V). For example, when the 5"-amino-protecting group is a Boc group, it is convenient to dissolve the 5"-N-protected caprazol-1'''-amide derivative in methanol containing 80% trifluoroacetic acid (TFA) and stir the solution at room temperature. The resulting reaction mixture is concentrated and diethyl ether is added to the syrup-like concentrate to form a precipitate. The precipitate is then collected by filtration, washed with diethyl ether and dried to give an addition salt of bis-trifluoroacetic acid of caprazol-1'''-amide derivative of the aforementioned general formula (V) as a solid.

While the caprazamycin derivatives represented by the aforementioned general formula (V) exhibit antibacterial activity against a wide range of bacteria and may preferably be used as antibacterial agents against bacteria in general, they are particularly useful as antibacterial agents against *Mycobacterium avium* subsp. *paratuberculosis*.

<Caprazamycin Derivative Represented by the General Formula (VI)>

Caprazamycin derivatives represented by the following general formula (VI) are amide and ester derivatives of caprazol represented by the aforementioned formula (IV). Specifically, they are caprazol-1'''-amide-3'''-ester derivatives.

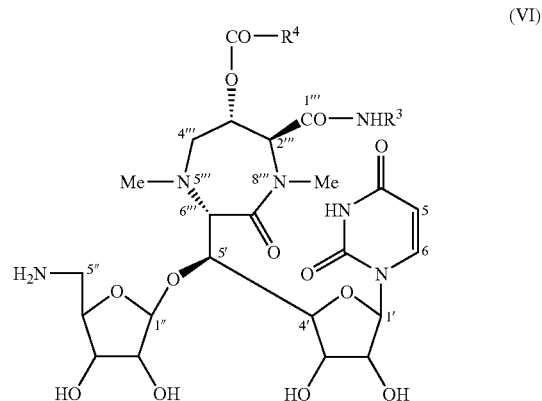

(VI)

wherein Me is a methyl group; and $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms.

The details of the straight or substantially straight chain alkyl group having 5 to 21 carbon atoms, the straight or substantially straight chain alkenyl group having 5 to 21 carbon atoms, or the cycloalkyl group having 5 to 12 carbon atoms are as defined for the alkyl group, alkenyl group and cycloalkyl group represented by $R^1$ in the aforementioned general formula (II), respectively.

$R^4$ in the aforementioned general formula (VI) is a straight or substantially straight chain alkyl group having 5 to 21 carbon atoms, a straight or substantially straight chain alkenyl group having 5 to 21 carbon atoms, or an alkynyl group having 5 to 21 carbon atoms. The details of $R^4$ are as defined for $R^2$ in the aforementioned general formula (III).

Specific examples of the caprazamycin derivatives represented by the aforementioned general formula (VI) are presented in Tables 7 below, along with their respective specific rotations.

TABLE 7

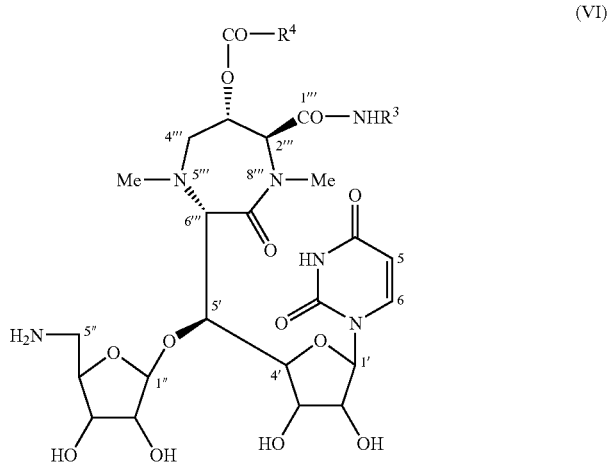

| Compound codes | $R^3$ in the formula (VI) | $R^4$ in the formula (VI) | Specific rotation $[\alpha]_D^{21}$ (c 0.5, in methanol) |
| --- | --- | --- | --- |
| Compound VI-A | —$(CH_2)_5CH_3$ | —$(CH_2)_5CH_3$ | +6° |
| Compound VI-B | —$(CH_2)_6CH_3$ | —$(CH_2)_6CH_3$ | |
| Compound VI-C | —$(CH_2)_7CH_3$ | —$(CH_2)_7CH_3$ | +6° |
| Compound VI-D | —$(CH_2)_8CH_3$ | —$(CH_2)_8CH_3$ | |
| Compound VI-E | —$(CH_2)_9CH_3$ | —$(CH_2)_9CH_3$ | +5° |
| Compound VI-F | —$(CH_2)_{10}CH_3$ | —$(CH_2)_{10}CH_3$ | +6° |
| Compound VI-G | —$(CH_2)_{11}CH_3$ | —$(CH_2)_{10}$—$CH_3$ | +6° |
| Compound VI-Q | cyclododecyl | —$(CH_2)_{10}$—$CH_3$ | +24° |
| Compound VI-R | —$(CH_2)_8CH$=$CH(CH_2)_7CH_3$ (cis form) | —$(CH_2)_{10}$—$CH_3$ | +5° |

(Production Process of Caprazamycin Derivatives Represented by the General Formula (VI))

Although the caprazamycin derivatives represented by the aforementioned general formula (VI) may be produced using any suitable known process, they are preferably produced as follows: First, 5"-N-alkoxycarbonyl- or 5"-N-aralkyloxycarbonyl-caprazol is prepared as described above in the production process of caprazamycin derivatives of the aforementioned general formula (V). The 5"-N-alkoxycarbonyl- or 5"-N-aralkyloxycarbonyl-caprazol is then dissolved in N,N-dimethylformamide. To this solution, 2,2-dimethoxypropane and an acid catalyst are added and the reaction is carried out at room temperature. This gives 5"-N-alkoxycarbonyl-2',3'; 2",3"-di-O-isopropylidene-caprazol or 5"-N-aralkyloxycarbonyl-2',3';2",3"-di-O-isopropylidene-caprazol in which each of the hydroxyl groups at the 2'- and 3'-positions and the hydroxyl groups at the 2"- and 3"-positions is protected by an isopropylidene group (=$C(CH_3)_2$, a known hydroxyl-protecting group). Anhydrous (±)-camphor-10-sulfonic acid may be conveniently used as the acid catalyst. Aqueous ammonia is then added to the reaction mixture and the mixture is concentrated. The resulting residue is extracted with n-butanol. Washing the extract with water and concentrating the extract gives desired 5"-N-alkoxycarbonyl-2',3';2",3"-di-O-isopropylidene-caprazol or 5"-N-aralkyloxycarbonyl-2', 3';2",3"-di-O-isopropylidene-caprazol as a solid (hereinafter, these products may be collectively referred to as "caprazol-N,O-protected derivative").

The caprazol-N,O-protected derivative is then dissolved in N,N-dimethylformamide. To this solution, triethylamine and then an amine compound represented by the aforementioned general formula (XIII) are added. An amidation process is carried out at room temperature and the reaction product is treated and purified as in the production of the caprazol-1'''-amide derivative represented by the aforementioned general formula (XIII) to give a desired caprazol-N,O-protected-1'''-amide derivative as a solid.

Subsequently, the caprazol-N,O-protected-1'''-amide derivative is dissolved in dichloromethane. To this solution, 4-dimethylaminopyridine and an acid chloride represented by the following general formula (XVI) are added and the reaction is carried out while the reaction mixture is chilled in an ice bath. This results in the acylation of the hydroxyl group at the 3'''-position by the acid chloride.

To the reaction mixture resulting from the acylation process, a small amount of methanol is added to decompose the remaining reagents. The mixture is then diluted with chloroform and the resulting solution is washed sequentially with an aqueous potassium hydrogen sulfate solution and water. The washed solution is dried and concentrated and the resulting residue is dissolved in chloroform. The solution is subjected to silica gel column chromatography for purification using a mixed solvent of chloroform-methanol as a developing solvent. The eluted active fractions are collected and concentrated to give caprazol-N,O-protected-1'''-amide-3'''-ester derivative as a solid.

The caprazol-N,O-protected-1'''-amide-3'''-ester derivative so obtained is treated by a common process for the elimination of amino-protecting groups to eliminate the 5"-amino-protecting group. Treating the resulting product with trifluoroacetic acid in methanol can eliminate the two isopropylidene groups protecting hydroxyl groups, thus giving a caprazol-1'''-amide-3'''-ester derivative represented by the aforementioned general formula (VI). Specifically, when the 5"-amino-protecting group is a Boc group, the Boc group and the two isopropylidene groups protecting hydroxyl groups can be conveniently eliminated at once by dissolving the caprazol-N,O-protected-1'''-amide-3'''-ester derivative in methanol containing 80% trifluoroacetic acid and stirring the solution at room temperature. The resulting reaction mixture is concentrated and diethyl ether is added to the syrup-like concentrate to form a precipitate. The precipitate is then collected by filtration, washed with diethyl ether and dried to give an addition salt of bis-trifluoroacetic acid of caprazol-1'''-amide-3'''-ester derivative represented by the aforementioned general formula (VI) as a solid.

While the caprazamycin derivatives represented by the aforementioned general formula (VI) exhibit antibacterial activity against a wide range of bacteria and may preferably be used as antibacterial agents against bacteria in general, they are particularly useful as antibacterial agents against *Mycobacterium avium* subsp. *paratuberculosis*.

<Caprazamycin Derivative Represented by the General Formula (VII)>

Caprazamycin derivatives represented by the following general formula (VII) are ester derivatives of caprazol represented by the aforementioned formula (IV). Specifically, they are caprazol-3'''-ester derivatives or caprazol-1'''-ester-3'''-ester derivatives.

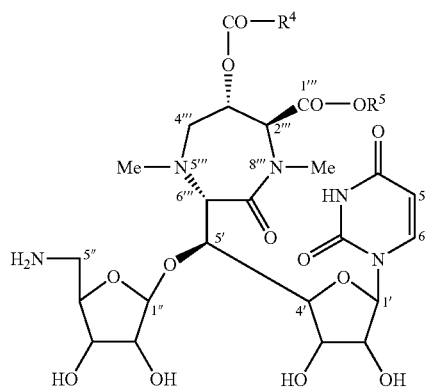

(VII)

wherein Me is a methyl group; and $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms. The details of $R^4$ are as defined for the aforementioned general formula (VI).

$R^5$ in the aforementioned general formula (VII) is a hydrogen atom or a straight or substantially straight chain alkyl group having 1 to 21 carbon atoms.

Examples of the straight chain alkyl group having 1 to 21 carbon atoms include methyl group, ethyl group, propyl group, butyl group and alkyl groups shown in the aforementioned Table 1.

Examples of the substantially straight chain alkyl group having 1 to 21 carbon atoms include alkyl groups having 5 to 21 carbon atoms whose straight carbon chain is substituted with 1 to 3 methyl, ethyl or n-propyl groups either at the terminal or at an internal carbon atom. Specific examples of such alkyl groups include 9-methyl-undecyl group (—$(CH_2)_8$CH($CH_3$)$CH_2CH_3$) and 10-methyl-undecyl group (—$(CH_2)_9$CH($CH_3$)$_2$).

Specific examples of the caprazamycin derivatives represented by the aforementioned general formula (VII) are presented in Tables 8 below, along with their respective specific rotations.

TABLE 8

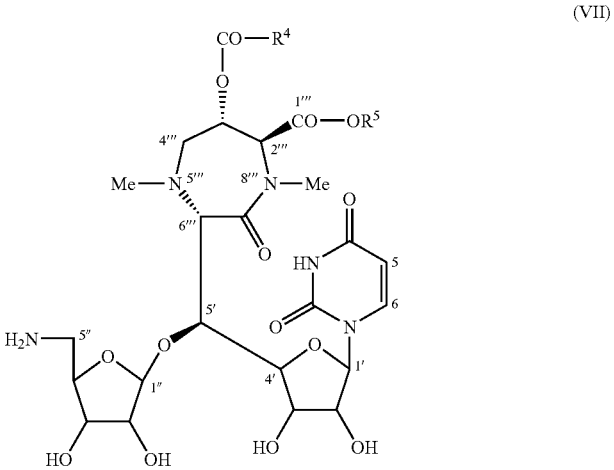

(VII)

| Compound codes | $R^4$ in the formula (VII) | $R^5$ in the formula (VII) | Specific rotation $[\alpha]_D^{20}$ |
|---|---|---|---|
| Compound VII-A | —$(CH_2)_5CH_3$ | —H | +16° (c 0.5, DMSO) |
| Compound VII-B | —$(CH_2)_6CH_3$ | —H | +16° (c 0.5, DMSO) |
| Compound VII-C | —$(CH_2)_7CH_3$ | —H | +16° (c 0.5, DMSO) |
| Compound VII-D | —$(CH_2)_8CH_3$ | —H | +17° (c 0.5, DMSO) |
| Compound VII-E | —$(CH_2)_9CH_3$ | —H | +17° (c 0.5, DMSO) |
| Compound VII-F | —$(CH_2)_{10}CH_3$ | —H | +17° (c 0.5, DMSO) |
| Compound VII-G | —$(CH_2)_{10}CH_3$ | —$CH_3$ | +6° (c 1, methanol) |

TABLE 8-continued

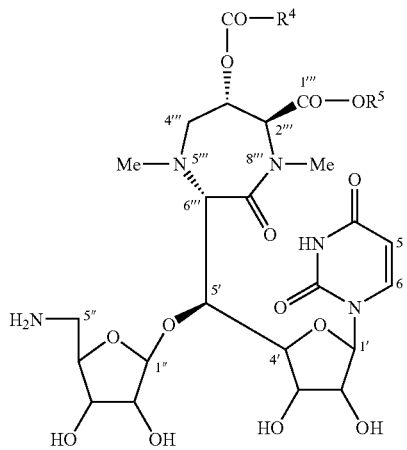

(VII)

| Compound codes | R⁴ in the formula (VII) | R⁵ in the formula (VII) | Specific rotation [α]$_D^{20}$ |
|---|---|---|---|
| Compound VII-Q | cyclododecyl | —H | |
| Compound VII-R | —CH$_2$)$_7$CH=CH(CH$_2$)$_7$CH$_3$ (cis form) | —H | +14° (c 0.5, DMSO) |

(Production Process of Caprazamycin Derivatives Represented by the General Formula (VII))

Although the caprazamycin derivatives represented by the aforementioned general formula (VII) may be produced using any suitable known process, they are preferably produced as follows: First, 5"-N-alkoxycarbonyl-2',3';2"',3"'-di-O-isopropylidene-caprazol or 5"-N-aralkyloxycarbonyl-2', 3';2"',3"'-di-O-isopropylidene-caprazol is prepared as described above in the production process of caprazamycin derivatives of the aforementioned general formula (VI). The caprazol-N,O-protected derivative is then dissolved in dichloromethane. To this solution, 4-dimethylaminopyridine and an acid chloride represented by the aforementioned general formula (XVI) are added and an acylation process is carried out as in the production of caprazamycin derivatives of the aforementioned general formula (VI) with the reaction mixture chilled in an ice bath. This results in the acylation of the hydroxyl group at the 3"'-position by the acid chloride. To the resulting reaction mixture, a small amount of methanol is added to decompose the remaining reagents. Subsequently, the mixture is diluted with chloroform and the resulting solution is washed sequentially with an aqueous potassium hydrogen sulfate solution and water. The washed solution is dried and concentrated to give a caprazol-N,O-protected-3"'-ester derivative as a solid.

The so-obtained caprazol-N,O-protected-3"'-ester derivative is treated by a common process for the elimination of amino-protecting groups to eliminate the 5"-amino-protecting group. Subsequently treating the resulting product with trifluoroacetic acid in methanol can eliminate the two isopropylidene groups protecting hydroxyl groups, thus giving a caprazol-3"'-ester derivative represented by the aforementioned general formula (VII). Specifically, when the 5"-amino-protecting group is a Boc group, the Boc group and the two isopropylidene groups protecting hydroxyl groups can be conveniently eliminated at once by dissolving the caprazol-N,O-protected-3"'-ester derivative in methanol containing 80% trifluoroacetic acid and stirring the solution at room temperature. The resulting reaction mixture is concentrated and the residue is washed with diethyl ether to give an addition salt of trifluoroacetic acid of caprazol-3"'-ester derivative represented by the aforementioned general formula (VII).

In an alternative process, the caprazol-N,O-protected derivative is dissolved in N,N-dimethylformamide. To this solution, triethylamine and N,N-bis(2-oxo-3-oxazolidinyl) phosphinic chloride are added, along with an alkanol represented by the general formula (XX) below as an esterifying agent, and the reaction is carried out at room temperature. This results in the esterification of the carboxyl group at the 2"'-position and, thus, the formation of a caprazol-N,O-protected-1"'-ester derivative.

$$R^5\text{—OH} \qquad\qquad\qquad (XX)$$

The reaction mixture resulting from the esterification process is concentrated and the residue is extracted with chloroform. The chloroform extract is washed with water, dried and concentrated. The resulting residue is dissolved in chloroform and the solution is subjected to silica gel column chromatography for purification using a mixed solvent of chloroform-methanol as a developing solvent. The eluate fractions containing the desired product are concentrated to obtain a caprazol-N,O-protected-1"'-ester derivative as a solid.

The caprazol-N,O-protected-1"'-ester derivative is then dissolved in dichloromethane. To this solution, 4-dimethylaminopyridine and an acid chloride represented by the aforementioned general formula (XVI) are added and an acylation process is carried out as in the production of caprazamycin derivatives of the aforementioned general formula (VI) with the reaction mixture chilled in an ice bath. This results in the acylation of the hydroxyl group at the 3"'-position by the acid chloride. To the resulting reaction mixture, a small amount of methanol is added to decompose the remaining reagents. Subsequently, the mixture is diluted with chloroform and the resulting solution is washed sequentially with an aqueous potassium hydrogen sulfate solution and water. The washed solution is dried and concentrated to give a caprazol-N,O-protected-1"'-ester-3"'-ester derivative as a solid.

The so-obtained caprazol-N,O-protected-1'''-ester-3'''-ester derivative is treated by a common process for the elimination of amino-protecting groups to eliminate the 5''-amino-protecting group. Subsequently treating the resulting product with trifluoroacetic acid in methanol can eliminate the two isopropylidene groups protecting hydroxyl groups, thus giving a caprazol-1'''-ester-3'''-ester derivative represented by the aforementioned general formula (VII). Specifically, when the 5''-amino-protecting group is a Boc group, the Boc group and the two isopropylidene groups protecting hydroxyl groups can be conveniently eliminated at once by dissolving the caprazol-N,O-protected-1'''-ester-3'''-ester derivative in methanol containing 80% trifluoroacetic acid and stirring the solution at room temperature. The resulting reaction mixture is concentrated and the residue is washed with diethyl ether to give an addition salt of trifluoroacetic acid of caprazol-1'''-ester-3'''-ester derivative represented by the aforementioned general formula (VII).

While the caprazamycin derivatives represented by the aforementioned general formula (VII) exhibit antibacterial activity against a wide range of bacteria and may preferably be used as antibacterial agents against bacteria in general, they are particularly effective as antibacterial agents against *Mycobacterium avium* subsp. *paratuberculosis*.

The antibacterial agent of the present invention may be used in any manner that suits the desired purpose. For example, it may be added and mixed or dispersed into the system in which *Mycobacterium avium* subsp. *paratuberculosis* are present.

The antibacterial agent of the present invention is particularly suitable for use in a therapeutic agent of the present invention for Johne's disease, which is described below.

(Therapeutic Agent for Johne's Disease)

A therapeutic agent of the present invention for Johne's disease contains the above-described antibacterial agent of the present invention and other optional components.

The therapeutic agent of the present invention for Johne's disease may be mixed with a solid or liquid excipient to formulate a solid or liquid preparation for oral or parenteral administration (ex. intramuscular, intravenous, subcutaneous, rectal or percutaneous administration).

The solid preparation may be formulated as a tablet, capsule, granule, powder or fine grain and may be coated to make an enteric-coated preparation. The liquid preparation may be formulated by providing the antibacterial agent in the form of a physiologically acceptable salt and dissolving the salt in water.

The optional components include pharmaceutically acceptable additives that can be used to make the therapeutic agent.

Examples of the additive that can be added to an oral preparation include excipients, such as starch, lactose, sucrose, corn starch, crystalline cellulose, mannitol and maltitol; disintegrating agents, such as partially gelatinized starch, cross carmellose sodium, carboxymethyl starch sodium and low-substituted hydroxypropyl cellulose; and lubricants, such as stearic acid, magnesium stearate, calcium stearate, hydrogenated vegetable oil and talc.

Examples of the additive that can be added to an injection solution that is prepared upon use include excipients, such as sodium dihydrogen phosphate and sodium hydrogen phosphate, and soothing agents, such as chlorobutanol and xylocaine hydrochloride.

The amount of the antibacterial agent of the present invention in the therapeutic agent for Johne's disease is preferably in the range of 20 to 90 wt %, and more preferably in the range of 40 to 70 wt %. The antibacterial agent is particularly effective against Johne's disease when present in an amount within these ranges.

When the therapeutic agent of the present invention for Johne's disease is orally administered to cattle for the purpose of preventing the disease, it is preferably administered at a daily dose of 50 to 500 mg/kg of body weight, and more preferably at a daily dose of 100 to 300 mg/kg of body weight, although the dose may vary depending on the age of the animals and the severity of the disease and may not be limited to a particular dose range.

The dose for parenteral administration also varies depending on the age of the animals and the severity of the disease and may not be limited to a particular dose range. However, the composition is preferably administered at a daily dose of 10 to 150 mg/kg of body weight, and more preferably at a daily dose of 20 to 100 mg/kg of body weight when administered to cattle for the purpose of preventing the disease. It is preferably administered at a daily dose of 20 to 300 mg/kg of body weight, and more preferably at a daily dose of 50 to 200 mg/kg of body weight when administered to cattle for the treatment of the disease. When necessary, the daily dose may be delivered in 1 to 3 separate doses depending on the condition of the disease.

The therapeutic agent of the present invention for Johne's disease is highly safe and can effectively suppress the activity of *Mycobacterium avium* subsp. *paratuberculosis* by the action of a caprazamycin derivative of one of the aforementioned general formulas (II), (III), (V), (VI) and (VII) that serves as the active ingredient. In this manner, the composition can effectively prevent or treat Johne's disease.

EXAMPLES

The present invention will now be described with reference to examples, which are not intended to limit the invention in any way.

Production Example 1

Production of Caprazene-1'''-amide Derivative

Compounds II-D, II-H, II-N and II-Q shown in Table 2, Compound II-4 shown in Table 3, and Compounds II-21 and II-24 shown in Table 4 were synthesized according to a production process involving Steps (1) through (4), as described below.

(1) Production of Caprazene from Caprazamycin B

The reaction of Step (1) is as shown below. Specifically, 200 mg of caprazamycin B were dissolved in 6 mL of 80% aqueous acetic acid and the resulting solution was heated at 70° C. for 2 hours. Subsequently, the reaction mixture was concentrated and acetone was added to the syrup-like concentrate. The resulting precipitate was collected by filtration, washed with acetone and dried to afford 96.3 mg of caprazene as a colorless solid (99% yield).

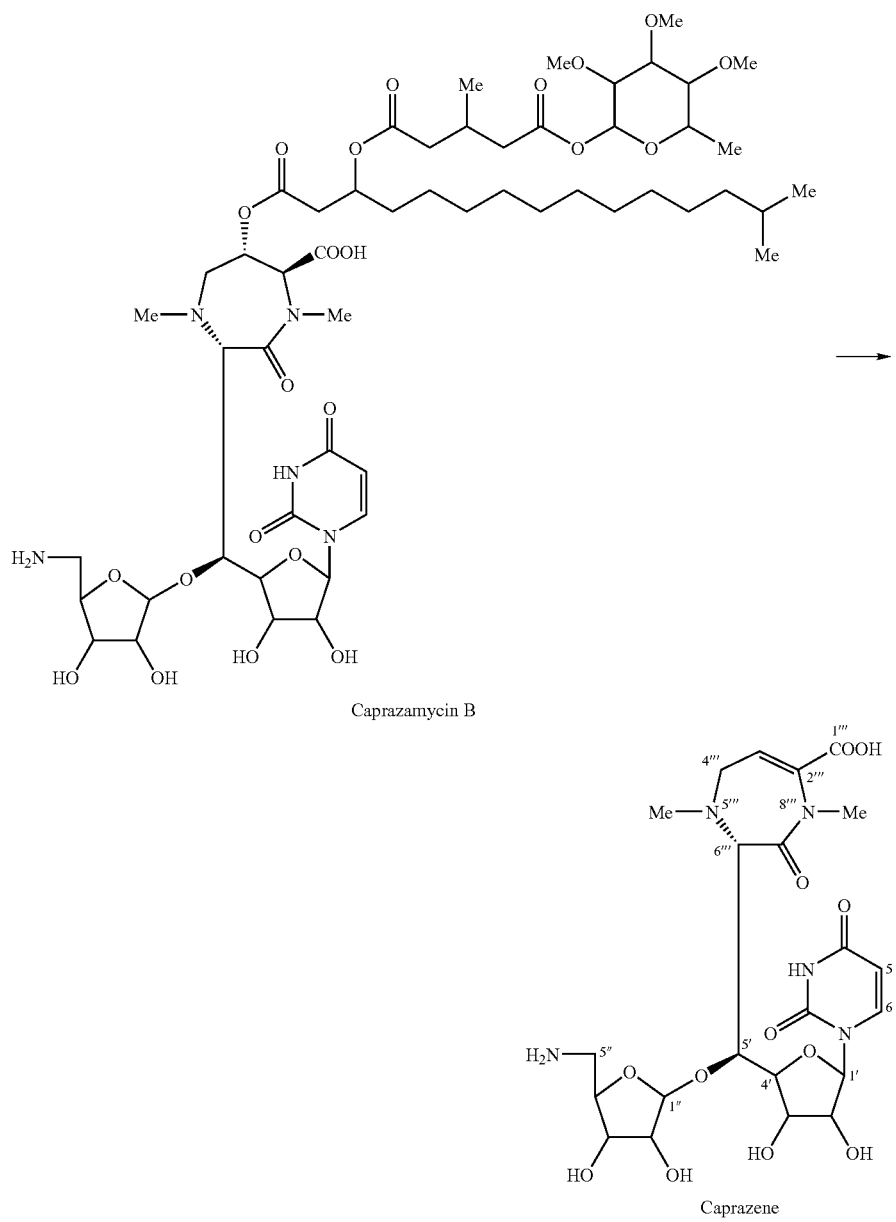

Caprazamycin B

Caprazene

The physicochemical properties of the resulting caprazene were determined to be as follows:

a) melting point: 210-211° C. (decomposed) (after crystallized from water-acetone),
b) specific rotation $[\alpha]_D^{19}$ +85° (c 0.5, H$_2$O),
c) $^1$H-NMR spectrum and $^{13}$C-NMR spectrum as shown in Table 9 below:

TABLE 9

| Position | $^1$H-NMR data for caprazene (δ, ppm in D$_2$O) | Position | $^{13}$C-NMR data for caprazene (δ, ppm in D$_2$O) |
|---|---|---|---|
| 5 | 5.82, d, J = 8 Hz | 2 | 151.7 |
| 6 | 7.69, d, J = 8 Hz | 4 | 166.8 |
| 1' | 5.62, d, J = 2.5 Hz | 5 | 102.0 |
| 2' | 4.28, dd, J = 2.5, 5 Hz | 6 | 142.4 |

TABLE 9-continued

| Position | $^1$H-NMR data for caprazene (δ, ppm in D$_2$O) | Position | $^{13}$C-NMR data for caprazene (δ, ppm in D$_2$O) |
|---|---|---|---|
| 3' | 4.12, dd, J = 5, ~8 Hz | 1' | 91.4 |
| 4' | 4.24, br. d, J = ~8 Hz | 2' | 73.9 |
| 5' | 4.34, dd, J = 2, 9.5 Hz | 3' | 69.4 |
| 1" | 5.22, slightly br. s | 4' | 82.7 |
| 2" | 4.13, br. d, J = ~5 Hz | 5' | 77.0 |
| 3" | 4.26, dd, J = ~5, ~8 Hz | 1" | 110.0 |
| 4" | 4.20, m | 2" | 75.3 |
| 5"a | 3.18, dd, J = 5, 14 Hz | 3" | 70.7 |
| 5"b | 3.35, dd, J = 4, 14 Hz | 4" | 79.0 |
| 2''' | | 5" | 40.5 |

TABLE 9-continued

| Position | $^1$H-NMR data for caprazene (δ, ppm in D$_2$O) | Position | $^{13}$C-NMR data for caprazene (δ, ppm in D$_2$O) |
|---|---|---|---|
| 3''' | 6.49, t, J = 7 Hz | 1''' | 169.2 |
| 4'''a | 2.94, dd, J = 7, 12.5 Hz | 2''' | 144.7 |
| 4'''b | 3.34, dd, J = 7, 12.5 Hz | 3''' | 123.5 |
| 6''' | 3.92, d, J = 9.5 Hz | 4''' | 51.5 |
| MeN-5''' | 2.42, s | 6''' | 63.6 (broad) |
| MeN-8''' | 2.99, s | 7''' | 171.3 |
| | | MeN-5''' | 40.5 |
| | | MeN-8''' | 33.2 |

(2) Production of 5''-N-Boc-caprazene from Caprazene

The reaction of Step (2) is as shown below. Specifically, 8.14 g of caprazene obtained in Step (1) were suspended in 120 ml of a mixed solvent of water-dioxane (2:1). To this suspension, 3.7 mL of triethyl amine were added to form a uniform solution of caprazene. To this solution, 3.2 g of di-t-butyl dicarbonate in 5 mL dioxane were added and the reaction was carried out at room temperature for 1 hour (introduction of t-butoxycarbonyl group as an amino-protecting group). Subsequently, the reaction mixture was concentrated and the resulting residue was washed with ethyl acetate and dried to afford 9.50 g of 5''-N-Boc-caprazene as a pale yellow solid (99% crude yield).

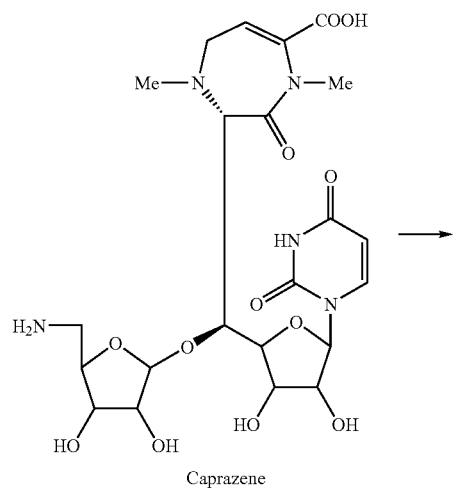

Caprazene

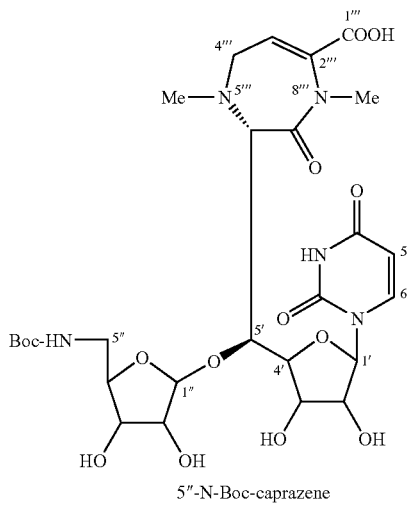

5''-N-Boc-caprazene $^1$H-NMR spectrum of the resulting 5''-N-Boc-caprazene was as follows (in deuterated water with TMS internal standard): δ 1.31 (9H, s, Me$_3$CO—), 2.39 (3H, slightly br. s, MeN-5'''), 2.98 (3H, s, MeN-8'''), 5.13 (1H, slightly br. s, H-1''), 5.62 (1H, slightly br. s, H-1'), 5.77 (1H, d, H-5, $J_{5,6}$=8 Hz), 6.44 (1H, t, H-3''', J=7 Hz), 7.77 (1H, d, H-6).

(3) Production of 5''-N-Boc-caprazene-1'''-amide Derivative from 5''-N-Boc-caprazene The reaction of Step (3) is as shown below. Specifically, 150 mg of 5''-N-Boc-caprazene obtained in Step (2) were suspended in 6 mL of tetrahydrofuran. To this suspension, 80 μL of triethyl amine and 80 mg of N,N-bis(2-oxo-3-oxazolidinyl)phosphinic chloride were added along with 1.1 to 1.3 molar equivalents of one of the different amine compounds (R$^1$—NH$_2$) shown in Table 10 below or one of the different para-substituted anilines shown in Table 11 below. The resulting mixture was stirred at room temperature for 1 hour to carry out the reaction (amidation process).

Subsequently, the reaction mixture was concentrated and the resulting syrup-like concentrate was extracted with chloroform. The chloroform extract was washed with water and concentrated. The resulting concentrate was dissolved in chloroform and the solution was subjected to silica gel column chromatography for purification (developing solvent=chloroform-methanol (10:1)). The eluted fraction was collected and concentrated. This gave 1'''-amide derivatives of 5''-N-Boc-protected forms of Compounds II-D, II-H, II-N and II-Q shown in Table 2, Compound II-4 shown in Table 3, and Compounds II-21 and II-24 shown in Table 4, each in the form of a colorless solid (91 to 128 mg, 50 to 60% yield in the preceding two steps from caprazene).

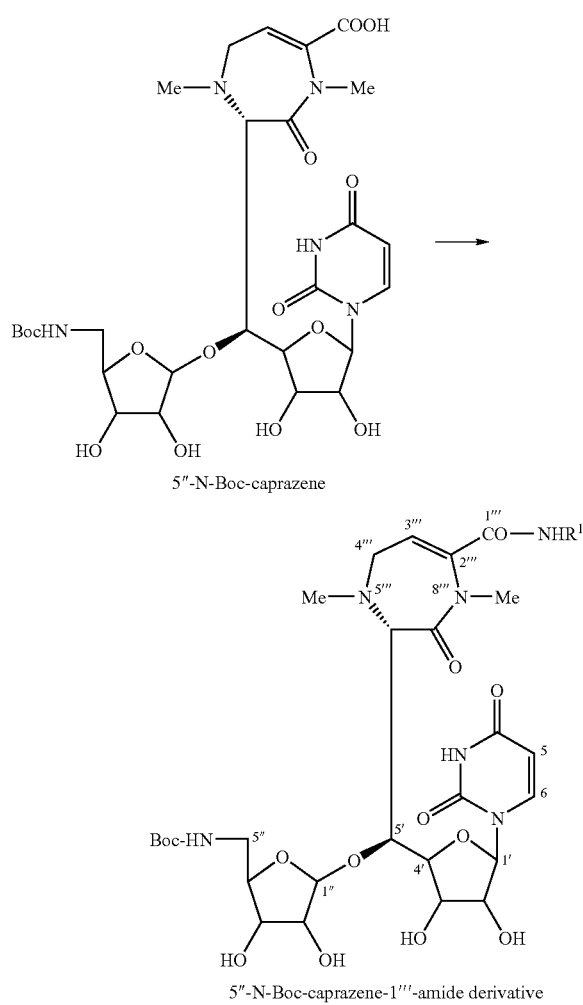

5″-N-Boc-caprazene

5″-N-Boc-caprazene-1‴-amide derivative

TABLE 10

| Compound codes of desired compounds | Amine compounds $R^1$—$NH_2$ | |
|---|---|---|
| (corresponding to Table 2) | Formula | Name |
| Compound II-D | $C_9H_{19}$—$NH_2$ | nonylamine |
| Compound II-H | $C_{13}H_{27}$—$NH_2$ | tridecylamine |
| Compound II-N | $C_{19}H_{38}$—$NH_2$ | nonadecylamine |
| Compound II-Q | | cyclododecylamine |

TABLE 11

| Compound codes of desired compounds (corresponding to Tables 3 and 4) | Para-substituted anilines $R^1$—$NH_2$ $R^1$ |
|---|---|
| Compound II-4 | —⌬—$(CH_2)_3CH_3$ |

TABLE 11-continued

| Compound codes of desired compounds (corresponding to Tables 3 and 4) | Para-substituted anilines $R^1$—$NH_2$ $R^1$ |
|---|---|
| Compound II-21 | —⌬—$O(CH_2)_6CH_3$ |
| Compound II-24 | —⌬—cyclohexyl |

(4) Production of Caprazene-1‴-amide Derivative from 5″-N-Boc-caprazene-1‴-amide Derivative The reaction of Step (4) is as shown below. Specifically, 50 mg of each of the 5″-N-Boc-caprazene-1‴-amide derivatives obtained in Step (3) were dissolved in 1 mL of a methanol solution of 80% trifluoroacetic acid. The reaction was carried out at room temperature for 1 hour to eliminate the amino-protecting group (Boc group). The reaction mixture resulting from the deprotection process was concentrated and diethyl ether was added to the resulting syrup-like concentrate. The precipitate obtained was washed with diethyl ether and dried to afford each of Compounds II-D, II-H, II-N and II-Q shown in Table 2, Compound II-4 shown in Table 3, and Compounds II-21 and II-24 shown in Table 4, each in the form of a colorless solid (54.5 to 57.0 mg, 96 to 99% yield as an addition salt of bis-trifluoroacetic acid).

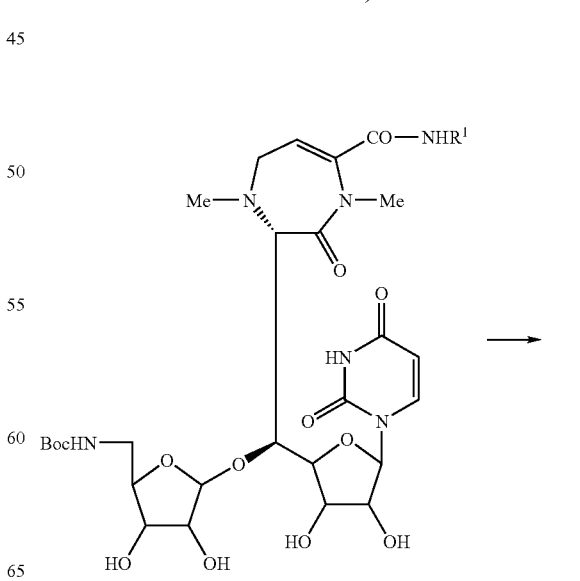

-continued

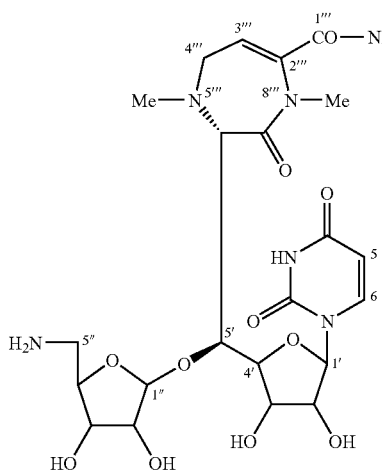

5''-N-Boc-caprazene-1'''-amide Derivative Caprazene-1'''-amide Derivative $^1$H-NMR spectra for Compounds II-D, II-H, II-N and II-Q (Table 2), Compound II-4 (Table 3) and Compounds II-21 and II-24 (Table 4), each a caprazene-1'''-amide derivative obtained in Step (4) of Production Example 1, are as follows (in deuterated dimethyl sulfoxide with TMS internal standard):

a) Compound II-D

δ 0.85 (3H, t, CH$_3$(CH$_2$)$_8$NH, J=7 Hz), 1.18-1.29 (12H, br. s, CH$_3$(CH$_2$)$_6$$\overline{CH_2}$CH$_2$NH), 2.34 (3H, br. s, MeN-5'''), 2.90 (3H, s, $\overline{MeN}$-8'''), 5.08 (1H, br. s, H-1''), 5.55 (1H, d, H-1', J=~1 Hz), 5.63 (1H, d, H-5, J=~8 Hz), 6.29 (1H, br. t, H-3''', J=~6 Hz), 7.68 (1H, br. d, H-6, J=~8 Hz), 11.32 (1H, s, NH-3).

b) Compound II-H

δ 0.86 (3H, t, CH$_3$(CH$_2$)$_{12}$NH, J=7 Hz), 1.18-1.30 (20H, br. s, CH$_3$(CH$_2$)$_{10}$$\overline{CH_2}$CH$_2$NH), 2.35 (3H, br. s, MeN-5'''), 2.90 (3H, s, $\overline{MeN}$-8'''), 5.09 (1H, br. s, H-1''), 5.55 (1H, d, H-1', J=~1 Hz), 5.63 (1H, d, H-5, J=~8 Hz), 6.29 (1H, br. t, H-3''', J=~6 Hz), 7.67 (1H, br. d, H-6, J=~8 Hz), 11.32 (1H, s, NH-3).

c) Compound II-N

δ 0.85 (3H, t, CH$_3$(CH$_2$)$_{18}$NH, J=7 Hz), 1.18-1.30 (32H, br. s, CH$_3$(CH$_2$)$_{16}$$\overline{CH_2}$CH$_2$NH), 2.34 (3H, br. s, MeN-5'''), 2.90 (3H, s, $\overline{MeN}$-8'''), 5.08 (1H, br. s, H-1''), 5.55 (1H, d, H-1', J=~2 Hz), 5.63 (1H, d, H-5, J=~8 Hz), 6.29 (1H, br. t, H-3''', J=~6 Hz), 7.68 (1H, br. d, H-6, J=~8 Hz), 11.32 (1H, s, NH-3).

d) Compound II-Q

δ 1.14-1.45 (22H, m, —(CH$_2$)$_{11}$—), 2.35 (3H, br. s, MeN-5'''), 2.91 (3H, s, MeN-8'''), 5.09 (1H, br. s, H-1''), 5.58 (1H, d, H-1', J=~2 Hz), 5.64 (1H, d, H-5, J=~8 Hz), 6.31 (1H, br. t, H-3''', J=~6 Hz), 7.66 (1H, br. d, H-6, J=~8 Hz), 11.33 (1H, s, NH-3).

e) Compound II-4

δ 0.89 (3H, t, CH$_3$(CH$_2$)$_3$C$_6$H$_4$NH, J=7.5 Hz), 2.38 (3H, br. s, MeN-5'''), 2.96 (3H, s, MeN-8'''), 5.12 (1H, br. s, H-1''), 5.60 (1H, d, H-1', J=2 Hz), 5.62 (1H, d, H-5, J=~8 Hz), 6.40 (1H, br. t, H-3''', J=~6 Hz), 7.14 and 7.52 (each 2H, d, CH$_3$(CH$_2$)$_3$$\overline{C_6H_4}$NH, J=8 Hz), 7.68 (1H, d, H-6, J=8 Hz), 10.15 (1H, s, $\overline{CH_3(CH_2)_3C_6H_4NH}$), 11.32 (1H, s, NH-3).

f) Compound II-21

δ 0.87 (3H, t, CH$_3$(CH$_2$)$_6$OC$_6$H$_4$NH, J=7 Hz), 2.37 (3H, br. s, MeN-5'''), 2.95 (3H, s, MeN-8'''), 5.11 (1H, br. s, H-1''), 5.60 (1H, d, H-1', J=2 Hz), 5.62 (1H, d, H-5, J=~8 Hz), 6.39 (1H, br. t, H-3''', J=~6 Hz), 6.88 and 7.50 (each 2H, d, CH$_3$(CH$_2$)$_6$OC$_6$H$_4$NH, J=9 Hz), 7.68 (1H, d, H-6, J=8 Hz), 10.07 (1H, s, $\overline{CH_3(CH_2)_6OC_6H_4NH}$), 11.32 (1H, s, NH-3).

g) Compound II-24

δ 2.37 (3H, br. s, MeN-5'''), 2.95 (3H, s, MeN-8'''), 5.11 (1H, br. s, H-1''), 5.59 (1H, d, H-1', J=2 Hz), 5.62 (1H, d, H-5, J=~8 Hz), 6.38 (1H, br. t, H-3''', J=~6 Hz), 7.16 and 7.52 (each 2H, d, —C$_6$H$_4$NH, J=9 Hz), 7.68 (1H, d, H-6, J=8 Hz), 10.14 (1H, s, —$\overline{C_6H_4NH}$), 11.32 (1H, s, NH-3).

Production Example 2

Production of Caprazol-3'''-ester Derivative

Compound VII-F shown in Table 8 was synthesized according to a production process involving Steps (1) through (5), as described below.

(1) Production of Caprazol from Caprazamycin B

The reaction of Step (1) is as shown below. Specifically, 150 mg of caprazamycin B were dissolved in 1.5 mL of N,N-dimethylformamide. To this solution, 1.5 mL of 28% aqueous ammonia were added and the resulting mixture was stirred at room temperature for 4 days for hydrolysis. The insoluble material developed in the reaction mixture was removed by filtration and the filtrate was concentrated. The resulting residue was washed with acetone and dried to afford 74.7 mg of caprazol as a colorless solid (99% yield).

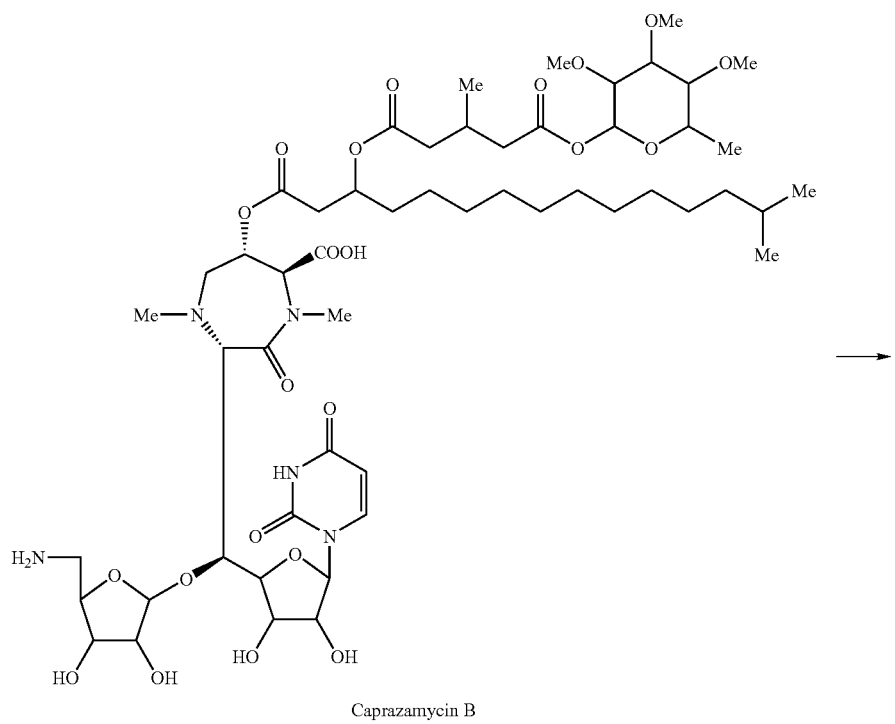

Caprazamycin B

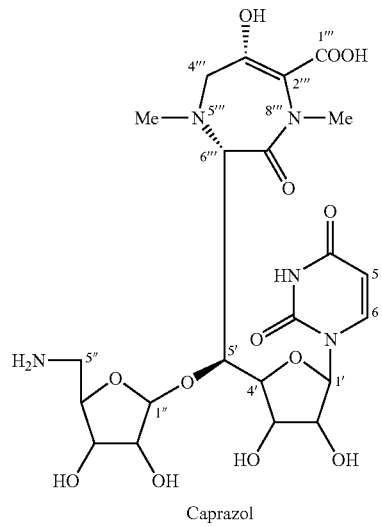

Caprazol

The physicochemical properties of the resulting caprazol were determined to be as follows:

a) melting point: 205-206° C. (decomposed) (after crystallized from water-methanol),
b) specific rotation $[\alpha]_D^{19}$ +28° (c 0.5, dimethyl sulfoxide),
c) $^1$H-NMR spectrum and $^{13}$C-NMR spectrum of caprazol are as shown in Table 12 below:

TABLE 12

| Position | $^1$H-NMR data for caprazol (δ, ppm in D$_2$O) | Position | $^{13}$C-NMR data for caprazol (δ, ppm in D$_2$O) |
|---|---|---|---|
| 5 | 5.82, d, J = 8 Hz | 2 | 151.8 |
| 6 | 7.77, d, J = 8 Hz | 4 | 167.1 |
| 1' | 5.60, slightly br. s | 5 | 101.7 |

TABLE 12-continued

| Position | $^1$H-NMR data for caprazol (δ, ppm in D$_2$O) | Position | $^{13}$C-NMR data for caprazol (δ, ppm in D$_2$O) |
|---|---|---|---|
| 2' | 4.31, br. d, J = 5 Hz | 6 | 142.9 |
| 3' | 4.08, dd, J = 5, 8 Hz | 1' | 91.8 |
| 4' | 4.13, d, J = ~8 Hz | 2' | 74.0 |
| 5' | 4.39, d, J = 9 Hz | 3' | 69.3 |
| 1" | 5.17, slightly br. s | 4' | 82.4 |
| 2" | 4.14, d, J = ~3 Hz | 5' | 77.6 |
| 3" | 4.25, m | 1" | 111.2 |
| 4" | ~4.21, m | 2" | 75.4 |
| 5"a | 3.20, dd, J = 4, 13.5 Hz | 3" | 70.6 |
| 5"b | 3.32, dd, J = 3.5, 13.5 Hz | 4" | 79.0 |
| 2''' | 4.20, d, J = ~5 Hz | 5" | 40.2 |
| 3''' | 4.44, br. s | 1''' | 174.1 |

TABLE 12-continued

| Position | $^1$H-NMR data for caprazol (δ, ppm in D$_2$O) | Position | $^{13}$C-NMR data for caprazol (δ, ppm in D$_2$O) |
|---|---|---|---|
| 4'''a | 3.01, br. d, J = 15 Hz | 2''' | 70.0 |
| 4'''b | 3.13, br. d, J = 15 Hz | 3''' | 69.3 |
| 6''' | 3.85, d, J = 9 Hz | 4''' | 59.1 |
| MeN-5''' | 2.43, s | 6''' | 63.5 |
| MeN-8''' | 3.07, s | 7''' | 172.7 |
| | | MeN-5''' | 37.0 |
| | | MeN-8''' | 39.2 |

(2) Production of 5''-N-Boc-caprazol from Caprazol 2.80 g of caprazol obtained in Step (1) were dissolved in 80 ml of a mixed solvent of water-dioxane (1:2). To this solution, 1.7 mL of triethyl amine and 1.27 g of di-t-butyl dicarbonate in 5 mL dioxane were added and the reaction was carried out at room temperature for 1 hour. Subsequently, the reaction mixture was concentrated and the resulting residue was washed with ethyl acetate and dried to afford 3.19 g of 5''-N-Boc-caprazol as a pale yellow solid (97% crude yield).
$^1$H-NMR spectrum of the resulting 5''-N-Boc-caprazol was as follows (in deuterated water):
δ 1.40 (9H, s, Me$_3$CO—), 2.47 (3H, s, MeN-5'''), 3.13 (3H, s, MeN-8'''), 5.16 (1H, s, H-1''), 5.74 (1H, br. s, H-1').

(3) Production of 5''-N-Boc-2',3';2'',3''-di-O-isopropylidene-caprazol from 5''-N-Boc-caprazol 3.19 g of 5''-N-Boc-caprazol obtained in Step (2) were dissolved in 60 mL of N,N-dimethylformamide. To this solution, 3.29 g of (±)-camphor-10-sulfonic acid and 17 mL of 2,2-dimethoxypropane were added and the reaction was carried out at room temperature overnight (introduction of O-isopropylidene group).
Subsequently, 0.5 mL of concentrated aqueous ammonia was added to neutralize the reaction mixture and the neutralized mixture was concentrated. The resulting residue was dissolved in n-butanol and the organic layer was washed with water, concentrated under reduced pressure and then dried to afford 3.55 g of 5''-N-Boc-2',3';2'',3''-di-O-isopropylidene-caprazol (99% yield).
The physicochemical properties of the resulting 5''-N-Boc-2',3';2'',3''-di-O-isopropylidene-caprazol were determined to be as follows:
a) specific rotation $[\alpha]_D^{19}$ −30° (c2, chloroform),
b) $^1$H-NMR spectrum (in deuterated methanol): δ 1.25, 1.36, 1.40, 1.53 (each 3H, s, methyl of isopropylidene), 1.45 (9H, s, Me$_3$CO—), 2.50 (3H, s, MeN-5'''), 3.09 (3H, s, MeN-8'''), 5.24 (1H, s, H-1''), 5.83 (1H, d, H-1', J=2.7 Hz).

(4) Production of 5''-N-Boc-2',3';2'',3''-di-O-isopropylidene-caprazol-dodecanoyl Ester Derivative from 5''-N-Boc-2',3';2'',3''-di-O-isopropylidene-caprazol 42 mg of 5''-N-Boc-2',3';2'',3''-di-O-isopropylidene-caprazol obtained in Step (3) were dissolved in 0.84 mL of dichloromethane. While this solution was chilled in an ice bath, 13.6 mg of 4-dimethylaminopyridine and 0.019 mL of dodecanoyl chloride (Cl—CO—(CH$_2$)$_{10}$—CH$_3$) to serve as an acylating agent were added. The reaction was carried out while the reaction mixture was chilled in an ice bath (3'''-O-esterification). During the course of the reaction, additional 13.6 mg of 4-dimethylaminopyridine and 0.019 mL of dodecanoyl chloride were added after 7 hours, followed by 11.2 mg of 4-dimethylaminopyridine and 0.019 mL of dodecanoyl chloride after 24 hours, and 11.9 mg of 4-dimethylaminopyridine and 0.019 mL of dodecanoyl chloride after 36 hours.

After 48 hours of esterification, 0.017 mL of methanol were added to the reaction mixture and the mixture was diluted with chloroform. The mixture was then washed sequentially with a 10% aqueous potassium hydrogen sulfate solution and water and dried over anhydrous sodium sulfate. Concentrating the resulting mixture gave 82.7 mg of a solid containing a 5''-N-Boc-2',3';2'',3''-di-O-isopropylidene-caprazol-dodecanoyl ester derivative.

(5) Production of Caprazol-3'''-dodecanoyl Ester Derivative from 5''-N-Boc-2',3';2'',3''-di-O-isopropylidene-caprazol-dodecanoyl Ester Derivative The solid (82.7 mg) containing 5''-N-Boc-2',3';2'',3''-di-O-isopropylidene-caprazol-dodecanoyl ester derivative obtained in Step (4) was dissolved in 0.85 mL of a mixture of trifluoroacetic acid-methanol (8:2) and the reaction was carried out at room temperature for 2.5 hours (deprotection). Subsequently, the reaction mixture was concentrated and diethyl ether was added to the residue. The resulting insoluble material was washed with diethyl ether to obtain 28.8 mg of a solid. The solid product was suspended in water and the suspension was passed through a DIAION HP-20 column. The column was washed with water and eluted sequentially with 50% aqueous methanol, 80% aqueous methanol and methanol. The eluted fraction containing the desired product was concentrated to afford 10.4 mg of caprazol-3'''-dodecanoyl ester derivative (25% yield based on the compound obtained in Step (4)).

The physicochemical properties of the resulting caprazol-3'''-dodecanoyl ester derivative were determined to be as follows:
a) specific rotation $[\alpha]_D^{20}$+17° (c 0.5, dimethyl sulfoxide),
b) $^1$H-NMR spectrum (in deuterated dimethyl sulfoxide): δ 0.86 (3H, t, (CH$_2$)$_{10}$Me, J=7 Hz), 2.26 (3H, s, MeN-5'''), 2.93 (3H, s, MeN-8'''), $\overline{5.00}$ (1H, s, H-1''), 5.40 (1H, br. s, H-3'''), 5.56 (1H, s, H-1'), 5.64 (1H, d, H-5, J=8 Hz), 7.81 (1H, d, H-6).

Example 1

Evaluation of Antibacterial Activity

Each of the caprazamycin derivatives obtained in Production Examples 1 and 2 was analyzed for the minimum growth inhibitory concentration (MIC) (μg/mL) for different species and subspecies of acid-fast bacilli, as were caprazamycin B (CPZ-B) and an antituberculosis agent isoniazid (INH) as controls. The analysis was conducted by performing a serial dilution technique on agar medium according to The Japanese Society of Chemotherapy Standards.

Specifically, each bacterial species or subspecies was inoculated on the test compound-containing Middlebrook 7H10 agar medium supplemented with mycobactin J and having a composition given below. After a 3-week incubation period at 37° C., the growth of bacteria was determined. The results are shown in Table 13. In Table 13, a smaller number indicates higher antibacterial activity.

Composition of Middlebrook 7H10 Agar Medium Supplemented with Mycobactin J

| | |
|---|---|
| Middlebrook 7H10 agar (BD211422, Difco) | 19 g |
| glycerol | 5 mL |
| mycobactin J | 2 mg in 1 mL EtOH |
| purified water | 900 mL |
| OADC Enrichment (BD212240, Difco) | 100 mL |

TABLE 13

| Compound codes for test compounds | Minumum growth inhibitory conc. of test compounds (μg/ml) | | |
|---|---|---|---|
| (corresponding to Tables 2, 3, 4 and 8) | *M. bovis* BCG Japanese | *M. avium* subsp. *avium* ATCC25291 | *M. avium* subsp. *paratuberculosis* ATCC43015 |
| Compound II-D | 12.5 | 3.13 | 0.20 |
| Compound II-H | 6.25 | 3.13 | 0.10 |
| Compound II-N | 1.56 | 1.56 | 0.78 |
| Compound II-Q | 6.25 | 3.13 | 0.10 |
| Compound II-4 | 6.25 | 3.13 | 0.39 |
| Compound II-21 | 6.25 | 1.56 | 0.20 |
| Compound II-24 | 3.13 | 3.13 | 0.39 |
| Compound VII-F | 3.13 | 12.5 | 0.78 |
| CPZ-B | 6.25 | 12.5 | 3.13 |
| INH | 0.20 | >50 | >50 |

<Acid-Fast Bacilli Tested>

*Mycobacterium bovis*

*Mycobacterium avium* subsp. *avium*

*Mycobacterium avium* subsp. *paratuberculosis*

The results of Table 13 indicate that each of the caprazamycin derivatives obtained in Production Examples 1 and 2 exhibits remarkably higher antibacterial activity against *Mycobacterium avium* subsp. *paratuberculosis* than against *Mycobacterium bovis* or *Mycobacterium avium* subsp. *avium*. It has also been demonstrated that caprazamycin B and isoniazid used as controls show lower antibacterial activity against *Mycobacterium avium* subsp. *paratuberculosis* than any of the caprazamycin derivatives obtained in Production Examples 1 and 2.

The antibacterial agent of the present invention exhibits high antibacterial activity against *Mycobacterium avium* subsp. *paratuberculosis* and can therefore serve as an effective countermeasure against the bacteria. Administration of the antibacterial agent of the present invention to various subjects infected with *Mycobacterium avium* subsp. *paratuberculosis* offers a simple way to prevent or treat Johne's disease. The antibacterial agent of the present invention is thus suitable for use as a treatment for Johne's disease.

The therapeutic agent of the present invention for Johne's disease is particularly effective in the prevention and treatment of Johne's disease in cattle.

What is claimed is:

1. A method for inhibiting growth of *Mycobacterium avium* subsp. *paratuberculosis*, comprising applying a caprazamycin derivative represented by one of the following general formula (II), (III), (V), (VI) or (VII) to *Mycobacterium avium* subsp. *paratuberculosis*:

(II)

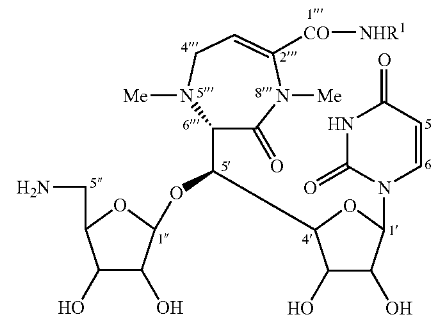

wherein Me is a methyl group; and $R^1$ is a straight or substantially straight chain alkyl group having 5 to 21 carbon atoms, a straight or substantially straight chain alkenyl group having 5 to 21 carbon atoms, a cycloalkyl group having 5 to 12 carbon atoms, or a phenyl group substituted at the para-position with a straight chain alkyl group having 1 to 14 carbon atoms, a straight chain alkoxy group having 1 to 9 carbon atoms or a cycloalkyl group having 5 to 12 carbon atoms;

(III)

wherein Me is a methyl group; and $R^2$ is a straight or substantially straight chain alkyl group having 5 to 21 carbon atoms, a straight or substantially straight chain alkenyl group having 5 to 21 carbon atoms, or an alkynyl group having 5 to 21 carbon atoms;

(V)

wherein Me is a methyl group; and $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms;

(VI)

wherein Me is a methyl group; $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms; and $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms; and (VII)

wherein Me is a methyl group; $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms; and $R^5$ is a hydrogen atom, or a straight or substantially straight chain alkyl group having 1 to 21 carbon atoms.

2. The method for inhibiting growth of *Mycobacterium avium* subsp. *paratuberculosis* according to claim 1, wherein the caprazamycin derivative is represented by the following general formula (II):

(II)

wherein Me is a methyl group; and $R^1$ is a straight or substantially straight chain alkyl group having 5 to 21 carbon atoms, a straight or substantially straight chain alkenyl group having 5 to 21 carbon atoms, a cycloalkyl group having 5 to 12 carbon atoms, or a phenyl group substituted at the para-position with a straight chain alkyl group having 1 to 14 carbon atoms, a straight chain alkoxy group having 1 to 9 carbon atoms, or a cycloalkyl group having 5 to 12 carbon atoms.

3. The method for inhibiting growth of *Mycobacterium avium* subsp. *paratuberculosis* according to claim 2, wherein $R^1$ is a straight chain alkyl group having 8 to 16 carbon atoms.

4. The method for inhibiting growth of *Mycobacterium avium* subsp. *paratuberculosis* according to claim 2, wherein $R^1$ is a cycloalkyl group having 5 to 12 carbon atoms, or a phenyl group substituted at the para-position with a straight chain alkyl group having 1 to 14 carbon atoms, a straight chain alkoxy group having 1 to 9 carbon atoms or a cycloalkyl group having 5 to 12 carbon atoms.

5. The method for inhibiting growth of *Mycobacterium avium* subsp. *paratuberculosis* according to claim 1, wherein the caprazamycin derivative is represented by the following general formula (III):

(III)

wherein Me is a methyl group; and $R^2$ is a straight or substantially straight chain alkyl group having 5 to 21 carbon atoms, a straight or substantially straight chain alkenyl group having 5 to 21 carbon atoms, or an alkynyl group having 5 to 21 carbon atoms.

6. The method for inhibiting growth of *Mycobacterium avium* subsp. *paratuberculosis* according to claim 1, wherein the caprazamycin derivative is represented by the following general formula (V):

(V)

wherein Me is a methyl group; and R³ is a straight or substantially straight chain alkyl group having 5 to 21 carbon atoms, a straight or substantially straight chain alkenyl group having 5 to 21 carbon atoms, or a cycloalkyl group having 5 to 12 carbon atoms.

7. The method for inhibiting growth of *Mycobacterium avium* subsp. *paratuberculosis* according to claim 1, wherein the caprazamycin derivative is represented by the following general formula (VI):

(VI)

wherein Me is a methyl group; R³ is a straight or substantially straight chain alkyl group having 5 to 21 carbon atoms, a straight or substantially straight chain alkenyl group having 5 to 21 carbon atoms, or a cycloalkyl group having 5 to 12 carbon atoms; and R⁴ is a straight or substantially straight chain alkyl group having 5 to 21 carbon atoms, a straight or substantially straight chain alkenyl group having 5 to 21 carbon atoms, or an alkynyl group having 5 to 21 carbon atoms.

8. The method for inhibiting growth of *Mycobacterium avium* subsp. *paratuberculosis* according to claim 1, wherein the caprazamycin derivative is represented by the following general formula (VII):

(VII)

wherein Me is a methyl group; R⁴ is a straight or substantially straight chain alkyl group having 5 to 21 carbon atoms, a straight or substantially straight chain alkenyl group having 5 to 21 carbon atoms, or an alkynyl group having 5 to 21 carbon atoms; and R⁵ is a hydrogen atom, or a straight or substantially straight chain alkyl group having 1 to 21 carbon atoms.

9. The method for inhibiting growth of *Mycobacterium avium* subsp. *paratuberculosis* according to claim 8, wherein R⁴ is a straight chain alkyl group having 8 to 16 carbon atoms; and R⁵ is a hydrogen atom.

10. A method for treatment of *Mycobacterium avium* subsp. *paratuberculosis* infection, comprising administrating a caprazamycin derivative represented by one of the following general formulae (II), (III), (V), (VI), or (VII) to a subject having *Mycobacterium avium* subsp. *paratuberculosis* infection:

(II)

wherein Me is a methyl group; and R¹ is a straight or substantially straight chain alkyl group having 5 to 21 carbon atoms, a straight or substantially straight chain alkenyl group having 5 to 21 carbon atoms, a cycloalkyl group having 5 to 12 carbon atoms, or a phenyl group substituted at the para-position with a straight chain alkyl group having 1 to 14 carbon atoms; a straight chain alkoxy group having 1 to 9 carbon atoms or a cycloalkyl group having 5 to 12 carbon atoms;

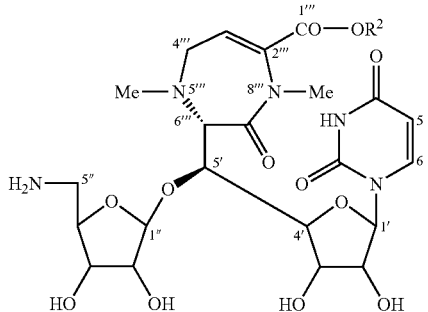
(III)

wherein Me is a methyl group; and $R^2$ is a straight or substantially straight chain alkyl group having 5 to 21 carbon atoms, a straight or substantially straight chain alkenyl group having 5 to 21 carbon atoms, or an alkynyl group having 5 to 21 carbon atoms;

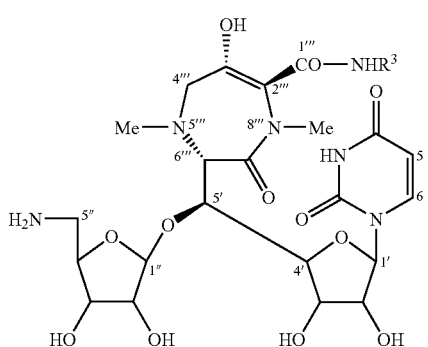
(V)

wherein Me is a methyl group; and $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms;

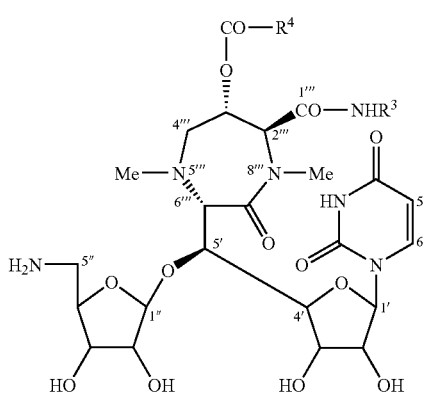
(VI)

wherein Me is a methyl group; $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms; and $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms; and

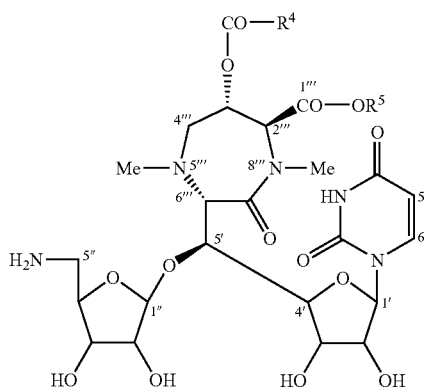
(VII)

wherein Me is a methyl group; $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms; and $R^5$ is a hydrogen atom, or a straight or substantially straight chain alkyl group having 1 to 21 carbon atoms.

11. The method for treatment of *Mycobacterium avium* subsp. *paratuberculosis* infection according to claim 10, wherein the caprazamycin derivative is represented by the following general formula

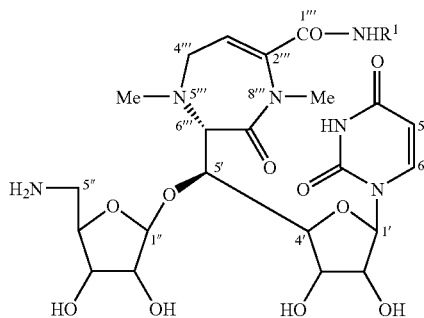
(II)

wherein Me is a methyl group; and $R^1$ is a straight or substantially straight chain alkyl group having 5 to 21 carbon atoms, a straight or substantially straight chain alkenyl group having 5 to 21 carbon atoms, a cycloalkyl group having 5 to 12 carbon atoms, or a phenyl group substituted at the para-position with a straight chain alkyl group having 1 to 14 carbon atoms, a straight chain alkoxy group having 1 to 9 carbon atoms, or a cycloalkyl group having 5 to 12 carbon atoms.

12. The method for treatment of *Mycobacterium avium* subsp. *paratuberculosis* infection according to claim 11, wherein $R^1$ is a straight chain alkyl group having 8 to 16 carbon atoms.

13. The method for treatment of *Mycobacterium avium* subsp. *paratuberculosis* infection according to claim 11, wherein $R^1$ is a cycloalkyl group having 5 to 12 carbon atoms, or a phenyl group substituted at the para-position with a straight chain alkyl group having 1 to 14 carbon atoms, a straight chain alkoxy group having 1 to 9 carbon atoms or a cycloalkyl group having 5 to 12 carbon atoms.

14. The method for treatment of *Mycobacterium avium* subsp. *paratuberculosis* infection according to claim 10, wherein the caprazamycin derivative is represented by the following general formula (III)

wherein Me is a methyl group; and $R^2$ is a straight or substantially straight chain alkyl group having 5 to 21 carbon atoms, a straight or substantially straight chain alkenyl group having 5 to 21 carbon atoms, or an alkynyl group having 5 to 21 carbon atoms.

15. The method for treatment of *Mycobacterium avium* subsp. *paratuberculosis* infection according to claim 10, wherein the caprazamycin derivative is represented by the following general formula (V)

wherein Me is a methyl group; and $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms.

16. The method for treatment of *Mycobacterium avium* subsp. *paratuberculosis* infection according to claim 10, wherein the caprazamycin derivative is represented by the following general formula (VI)

wherein Me is a methyl group; $R^3$ is a straight or substantially straight chain alkyl group having 5 to 21 carbon atoms, a straight or substantially straight chain alkenyl group having 5 to 21 carbon atoms, or a cycloalkyl group having 5 to 12 carbon atoms; and $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms.

17. The method for treatment of *Mycobacterium avium* subsp. *paratuberculosis* infection according to claim 10, wherein the caprazamycin derivative is represented by the following general formula (VII):

(VII)

wherein Me is a methyl group; $R^4$ is a straight or substantially straight chain alkyl group having 5 to 21 carbon atoms, a straight or substantially straight chain alkenyl group having 5 to 21 carbon atoms, or an alkynyl group having 5 to 21 carbon atoms; and $R^5$ is a hydrogen atom, or a straight or substantially straight chain alkyl group having 1 to 21 carbon atoms.

18. The method for treatment of *Mycobacterium avium* subsp. *paratuberculosis* infection according to claim 17, wherein $R^4$ is a straight chain alkyl group having 8 to 16 carbon atoms; and $R^5$ is a hydrogen atom.

19. The method for treatment of *Mycobacterium avium* subsp. *paratuberculosis* infection according to claim 10, wherein the *Mycobacterium avium* subsp. *paratuberculosis* infection includes Johne's disease.

\* \* \* \* \*

UNITED STATES PATENT AND TRADEMARK OFFICE
CERTIFICATE OF CORRECTION

PATENT NO. : 8,058,247 B2
APPLICATION NO. : 12/378172
DATED : November 15, 2011
INVENTOR(S) : Yoshiaki Takahashi et al.

It is certified that error appears in the above-identified patent and that said Letters Patent is hereby corrected as shown below:

Column 50, Line 31

Add -- (II): -- after the phrase "following general formula"

Column 51, Line 4

Add -- (III): -- after the phrase "following general formula"

Column 51, Line 37

Add -- (V): -- after the phrase "following general formula"

Column 51, Line 65

Add -- (VI): -- after the phrase "following general formula"

Signed and Sealed this
Thirty-first Day of January, 2012

David J. Kappos
*Director of the United States Patent and Trademark Office*